US006864066B1

(12) United States Patent
Chang et al.

(10) Patent No.: US 6,864,066 B1
(45) Date of Patent: Mar. 8, 2005

(54) EPITHELIAL PROTEIN LOST IN NEOPLASM (EPLIN)

(75) Inventors: David D. Chang, Calabasas, CA (US); Raymond S. Maul, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 313 days.

(21) Appl. No.: 09/658,400

(22) Filed: Sep. 8, 2000

Related U.S. Application Data

(60) Provisional application No. 60/153,024, filed on Sep. 8, 1999.

(51) Int. Cl.[7] .............................................. C12N 15/00
(52) U.S. Cl. .................... 435/69.1; 536/23.1; 536/23.5; 536/24.31; 435/320.1; 435/325
(58) Field of Search .............................. 536/23.5, 23.1, 536/24.31; 435/70.1, 320.1, 325, 252.1, 69.1; 530/350

(56) References Cited

U.S. PATENT DOCUMENTS

| 4,708,948 A | 11/1987 | Iwata et al. ..................... 514/2 |
| 6,262,334 B1 * | 7/2001 | Endege et al. ................. 800/8 |

OTHER PUBLICATIONS

Database GenBank, Accession No. AF157325, Ren, S, et al (Direct Submission), Jun. 9, 1999, Homo sapiens sterol regulatory element binding protein 3 (SREBP3) mRNA, complete cds.*
Database GenBank, Accession No. AC008147, Worley, KC (Direct Submission), Jul. 27, 1999, Homo sapiens 12 BAC RP3–405J10 (Roswell Park Cancer Inst. Human BAC Library) complete sequence.*
Database GenBank, Accession No. AA075396, Hillier, et al, 1996, Genome Research 6(9): 807–828 (EST Dec. 23, 1997), zm87d08.s1 Stratagene ovarian cancer (#937219) Homo Sapiens cDNA clone IMAGE:544911 3', mRNA sequence.*
Database GenBank, Accession No. AF198454, Maul, RS, et al (Direct Submission), Oct. 25, 1999, Homo sapiens epithelial protein lost in neoplasm beta (ELPIN) mRNA, complete cds.*
Database GenBank, Accession No. AQ314676, Adams, MD, et al (Unpublished), 1998 (EST May 4, 1999), RPCI11–103F24.TV RPCI–11 Homo sapiens genomic clone RPCI–11–103F24, DNA sequence.*
Maul, RS, et al, 2001, Gene 262: 155–160.*
Song, Y, et al, 2002, Molecular Biology of the Cell 13: 1408–1416.*
Kononen, J, et al, 1998, Nature Medicine 4 (7): 844–847.*
DeRisi, J, et al, 1996, Nature Genetics 14: 457–460.*
Moch, H, et al, 1999 Am J Pathol 154 (4): 981–986.*
Maul et al., "EPLIN, Epithelial protein lost in neoplasm," Oncogene, (1999) vol. 18, pp. 7838–7841.
Chen et al., "Characterization of the human EPLIN (Epithelial Protein Lost in Neoplasm) gene reveals distinct promoters for the two EPLIN isoforms," GENE, (2000) vol. 248, pp. 69–76.

* cited by examiner

*Primary Examiner*—Anthony C. Caputa
*Assistant Examiner*—Stephen L. Rawlings
(74) *Attorney, Agent, or Firm*—Fish & Richardson P.C.

(57) ABSTRACT

Polynucleotide and polypeptide sequences encoding a novel tumor suppressor protein, EPLIN, are provided. Also included is a method for detecting a cell proliferative disorder associated with EPLIN. EPLIN is a marker that can be used diagnostically, prognostically and therapeutically over the course of cell proliferative disorders associated with EPLIN.

23 Claims, 8 Drawing Sheets

(1 of 8 Drawing Sheet(s) Filed in Color)

```
...DKPAETKKLRIAWPPPTELGSSGSALEEGIKMSKPKWPPEDEISKPEVPEDVDLDLKKLR    579
...RSSSLKERSRPFTVAASFQSTSVKSPKTVSPPIRKGWSMSEQSEESVGGRVAERKQVENA    639
...KASKKNGNVGKTTWQNKESKGETGKRSKEGHSLEMENENIVENGADSDEDDNSFLKQQSP    699
...QEPKSLNWSSFVDNTFAEEFTTQNQKSQDVELWEGEVVKELSVEEQIKRNRYYDEDEDEE    759
```

FIG. 1B
*(Continued)*

```
EPLIN       CVECQKTVYPMERLLANQQVFHISCFRCSYCNNKLSLGTYASLH--GRIYCKPH
mtSREBP2    ..G................S.EGHF..RE........--Q.............
KIAA0750    .YF.K.R..V....S.EGHF..RE.....I.ATT.R..AA.TFDCDE.KF....
SF3         .TV.E....LVDK.V...R.Y.KA....HH..ST.K.SNFN.FD--..VV..RH.
MLP         .GA.E.....HA.EIQC.GRS...KT..H.MA.RKA.DST.V.AHE---SEI...VC
```

FIG. 1C

HOK18C(anti-EPLIN)

HOK18C(OG-Phalloidin)

BeWo(anti-EPLIN)

BeWo(TR-Phalloidin)

SEQUENCE LISTING

<160> NUMBER OF SEQ ID NOS: 10

<210> SEQ ID NO 1
<211> LENGTH: 3543
<212> TYPE: DNA
<213> ORGANISM: Homo sapiens

<400> SEQUENCE: 1

```
gctttctcca tgtggcaagg ctgtaactgt tcacagctgt ctgaaacagc agtggaccag      60
gagcagcttg gagttttaac tttcatttta caaagaacaa catgtttgaa tgtttcagca     120
ggcaagttat aactggcatc tacttcttgt tcttctagaa caccgaaaat ctctcccagc     180
actttagaaa ggggaccctg actgtgttaa agaagaagtg ggagaaccca gggctgggag     240
cagagtctca cacagactct ctacggaaca gcagcactga gattaggcac agagcagacc     300
atcctcctgc tgaagtgaca agccacgctg cttctggagc caaagctgac caagaagaac     360
aaatccaccc cagatctaga ctcaggtcac ctcctgaagc cctcgttcag ggtcgatatc     420
cccacatcaa ggacggtgag gatcttaaag accactcaac agaaagtaaa aaaatggaaa     480
attgtctagg agaatccagg catgaagtag aaaaatcaga aatcagtgaa aacacagatg     540
cttcgggcaa aatagagaaa tataatgttc cgctgaacag gcttaagatg atgtttgaga     600
```

-continued

```
aaggtgaacc aactcaaact aagattctcc gggcccaaag ccgaagtgca agtggaagga    660
agatctctga aaacagctat tctctagatg acctggaaat aggcccaggt cagttgtcat    720
cttctacatt tgactcggag aaaaatgaga gtagacgaaa tctggaactt ccacgcctct    780
cagaaacctc tataaaggat cgaatggcca agtaccaggc agctgcgtcc aaacaaagca    840
gctcaaccaa ctatacaaat gagctgaaag ccagtggtgg cgaaatcaaa attcataaaa    900
tggagcaaaa ggagaatgtg cccccaggtc ctgaggtctg catcacccat caggaagggg    960
aaaagatttc tgcaaatgag aatagcctgg cagtccgttc caccccctgcc gaagatgact   1020 ccccaggtga ctcccaggtt aagagtgagg ttcaacagcc tgtccatccc aagccactaa   1080
gtccagattc cagagcctcc agtctttctg aaagttctcc tcccaaagca atgaagaagt   1140
ttcaggcacc tgcaagagag acctgcgtgg aatgtcagaa acagtctat ccaatggagc    1200 gtctcttggc caaccagcag gtgtttcaca tcagctgctt ccgttgctcc tattgcaaca   1260
acaaactcag tctaggaaca tatgcatctt tacatggaag aatctattgt aagcctcact   1320
tcaatcaact cttttaaatct aagggcaact atgatgaagg cttttgggcac agaccacaca   1380 aggatctatg ggcaagcaaa aatgaaaacg aagagatttt ggagagacca gcccagcttg   1440
caaatgcaag ggagacccct cacagcccag gggtagaaaa tgcccctatt gctaaggtgg   1500
gtgtcctggc tgcaagtatg aagccaggg cctcctctca gcaggagaag gaagacaagc    1560
cagctgaaac caagaagctg aggatcgcct ggccaccccc cactgaactt ggaagttcag   1620
gaagtgcctt ggaggaaggg atcaaaatgt caaagcccaa atggcctcct gaagacgaaa   1680
tcagcaagcc cgaagttcct gaggatgtcg atctagatct gaagaagcta agacgatctt   1740
cttcactgaa ggaaagaagc cgcccattca ctgtagcagc ttcatttcaa agcacctctg   1800
tcaagagccc aaaaactgtg tccccaccta tcaggaaagg ctggagcatg tcagagcaga   1860
atgaagaatc tgtgggtgga agagttgcag aaaggaaaca agtggaaaat gccaaggctt   1920
ctaagaagaa tgggaatgtg ggaaaaacaa cctggcaaaa caaagaattt aaaggagaga   1980
cagggaagag aagtaaggaa ggtcatagtt tggagatgga gaatgagaat tttgtagaaa   2040
atggtgcaga ctccgatgaa gatgataaca gcttcctcaa acaacaattt ccacaagaac   2100
ccaagttttt gaattggtcg agttttgtag acaacacctt tgctgaagaa ttcactactc   2160
agaatcagaa atcccaggat gtggaacttt gggagggaga agtggtcaaa gagctctctg   2220
tggaagaaca gataaagaga atcggtatt atgatgagga tgaggatgaa gagtgacaaa   2280
ttgcaatgat gctgggcctt aaattcatgt tagtgttagc gagccactgc cctttgtcaa   2340
aatgtgatgc acataagcag gtatcccagc atgaaatgta atttacttgg aagtaacttt   2400
ggaaaagaat tccttcttaa aatcaaaaac aaaacaaaaa aacacaaaaa acacattcta   2460
aatactagag ataactttac ttaaattctt catcagtgat gatatgcata agtgctgtaa   2520
ggcttgtaac tggggaaata ttccacctga taatagccca gattctactg tattcccaaa   2580
aggcaatatt aagtagata gatgattagt agtatattgt tacacactat tttggaatta    2640
gagaacatac agaaggaatt tagggggctta acattacga ctgaatgcac tttagtataa   2700
agggcacagt ttgtatattt ttaaatgaat accaatttaa tttttagta tttacctgtt    2760 aagagattat ttagtctttta aattttttag gttaattttc ttgctgtgat atatatgagg   2820
aatttactac tttatgtcct gctctctaaa ctacatcctg aactcgacgt cctgaggtat   2880
aacaacagag cacttttgga ggcaattgaa aaaccaacct acactcttcg gtgcttagag   2940
```

-continued

```
agatctgctg tctcccaaat aagcttttgt atctgccagt gaatttactg tactccaaat    3000
gattgctttc ttttctggtg atatctgtgc ttctcataat tactgaaagc tgcaatattt    3060
tagtaatacc ttcgggatca ctgtccccca tcttccgtgt tagagcaaag tgaagagttt    3120
aaaggaggaa gaagaaagaa ctgtcttaca ccacttgagc tcagacctct aaaccctgta    3180
tttcccttat gatgtcccct ttttgagaca ctaattttta aatacttact agctctgaaa    3240
tatattgatt tttatcacag tattctcagg gtgaaattaa accaactata ggccttttc     3300
ttgggatgat tttctagtct taaggtttgg ggacattata aacttgagta catttgttgt    3360
acacagttga tattccaaat tgtatggatg ggagggagag gtgtcttaag ctgtaggctt    3420
ttctttgtac tgcatttata gagatttagc tttaatattt tttagagatg taaaacattc    3480
tgctttctta gtcttaccta gtctgaaaca tttttattca ataaagattt taattaaaat    3540
ttg                                                                  3543
```

<210> SEQ ID NO 2
<211> LENGTH: 600
<212> TYPE: PRT
<213> ORGANISM: Homo sapiens

<400> SEQUENCE: 2

```
Met Glu Asn Cys Leu Gly Glu Ser Arg His Glu Val Glu Lys Ser Glu
  1               5                  10                  15

Ile Ser Glu Asn Thr Asp Ala Ser Gly Lys Ile Glu Lys Tyr Asn Val
                 20                  25                  30

Pro Leu Asn Arg Leu Lys Met Met Phe Glu Lys Gly Glu Pro Thr Gln
             35                  40                  45

Thr Lys Ile Leu Arg Ala Gln Ser Arg Ser Ala Ser Gly Arg Lys Ile
         50                  55                  60

Ser Glu Asn Ser Tyr Ser Leu Asp Asp Leu Glu Ile Gly Pro Gly Gln
 65                  70                  75                  80

Leu Ser Ser Ser Thr Phe Asp Ser Glu Lys Asn Glu Ser Arg Arg Asn
                 85                  90                  95

Leu Glu Leu Pro Arg Leu Ser Glu Thr Ser Ile Lys Asp Arg Met Ala
            100                 105                 110

Lys Tyr Gln Ala Ala Val Ser Lys Gln Ser Ser Ser Thr Asn Tyr Thr
        115                 120                 125

Asn Glu Leu Lys Ala Ser Gly Gly Glu Ile Lys Ile His Lys Met Glu
    130                 135                 140

Gln Lys Glu Asn Val Pro Pro Gly Pro Glu Val Cys Ile Thr His Gln
145                 150                 155                 160

Glu Gly Glu Lys Ile Ser Ala Asn Glu Asn Ser Leu Ala Val Arg Ser
                165                 170                 175

Thr Pro Ala Glu Asp Asp Ser Pro Gly Asp Ser Gln Val Lys Ser Glu
            180                 185                 190

Val Gln Gln Pro Val His Pro Lys Pro Leu Ser Pro Asp Ser Arg Ala
        195                 200                 205

Ser Ser Leu Ser Glu Ser Ser Pro Pro Lys Ala Met Lys Lys Phe Gln
    210                 215                 220

Ala Pro Ala Arg Glu Thr Cys Val Glu Cys Gln Lys Thr Val Tyr Pro
225                 230                 235                 240

Met Glu Arg Leu Leu Ala Asn Gln Gln Val Phe His Ile Ser Cys Phe
                245                 250                 255

Arg Cys Ser Tyr Cys Asn Asn Lys Leu Ser Leu Gly Thr Tyr Ala Ser
```

```
                    260                 265                 270
Leu His Gly Arg Ile Tyr Cys Lys Pro His Phe Asn Gln Leu Phe Lys
            275                 280                 285

Ser Lys Gly Asn Tyr Asp Glu Gly Phe Gly His Arg Pro His Lys Asp
        290                 295                 300

Leu Trp Ala Ser Lys Asn Glu Asn Glu Glu Ile Leu Glu Arg Pro Ala
305                 310                 315                 320

Gln Leu Ala Asn Ala Arg Glu Thr Pro His Ser Pro Gly Val Glu Asp
                325                 330                 335

Ala Pro Ile Ala Lys Val Gly Val Leu Ala Ala Ser Met Glu Ala Lys
            340                 345                 350

Ala Ser Ser Gln Gln Glu Lys Glu Asp Lys Pro Ala Glu Thr Lys Lys
        355                 360                 365

Leu Arg Ile Ala Trp Pro Pro Pro Thr Glu Leu Gly Ser Ser Gly Ser
370                 375                 380

Ala Leu Glu Glu Gly Ile Lys Met Ser Lys Pro Lys Trp Pro Pro Glu
385                 390                 395                 400

Asp Glu Ile Ser Lys Pro Glu Val Pro Glu Asp Val Asp Leu Asp Leu
                405                 410                 415

Lys Lys Leu Arg Arg Ser Ser Ser Leu Lys Glu Arg Ser Arg Pro Phe
            420                 425                 430

Thr Val Ala Ala Ser Phe Gln Ser Thr Ser Val Lys Ser Pro Lys Thr
        435                 440                 445

Val Ser Pro Pro Ile Arg Lys Gly Trp Ser Met Ser Glu Gln Ser Glu
    450                 455                 460

Glu Ser Val Gly Gly Arg Val Ala Glu Arg Lys Gln Val Glu Asn Ala
465                 470                 475                 480

Lys Ala Ser Lys Lys Asn Gly Asn Val Gly Lys Thr Thr Trp Gln Asn
                485                 490                 495

Lys Glu Ser Lys Gly Glu Thr Gly Lys Arg Ser Lys Glu Gly His Ser
            500                 505                 510

Leu Glu Met Glu Asn Glu Asn Ile Val Glu Asn Gly Ala Asp Ser Asp
        515                 520                 525

Glu Asp Asp Asn Ser Phe Leu Lys Gln Gln Ser Pro Gln Glu Pro Lys
    530                 535                 540

Ser Leu Asn Trp Ser Ser Phe Val Asp Asn Thr Phe Ala Glu Glu Phe
545                 550                 555                 560

Thr Thr Gln Asn Gln Lys Ser Gln Asp Val Glu Leu Trp Glu Gly Glu
                565                 570                 575

Val Val Lys Glu Leu Ser Val Glu Gln Ile Lys Arg Asn Arg Tyr
            580                 585                 590

Tyr Asp Glu Asp Glu Asp Glu Glu
        595                 600

<210> SEQ ID NO 3
<211> LENGTH: 3650
<212> TYPE: DNA
<213> ORGANISM: Homo sapiens

<400> SEQUENCE: 3
ggcacgaggc gctaggtaga gcgccgggac ctgtgacagg gctggtagca gcgcacagga    60
aaggcggctt ttagccaggt atttcagtgt ctgtagacaa gatggaatca tctccattta   120
atagacggca atggacctca ctatcattga gggtaacagc caaagaactt tctcttgtca   180
```

-continued

| | |
|---|---|
| acaagaacaa gtcatcggct attgtggaaa tattctccaa gtaccagaaa gcagctgaag | 240 |
| aaacaaacat ggagaagaag agaagtaaca ccgaaaatct ctcccagcac tttagaaagg | 300 |
| ggaccctgac tgtgttaaag aagaagtggg agaacccagg gctgggagca gagtctcaca | 360 |
| cagactctct acggaacagc agcactgaga ttaggcacag agcagaccat cctcctgctg | 420 |
| aagtgacaag ccacgctgct tctggagcca aagctgacca agaagaacaa atccacccca | 480 |
| gatctagact caggtcacct cctgaagccc tcgttcaggg tcgatatccc cacatcaagg | 540 |
| acggtgagga tcttaaagac cactcaacag aaagtaaaaa aatggaaaat tgtctaggag | 600 |
| aatccaggca tgaagtagaa aaatcagaaa tcagtgaaaa cacagatgct tcgggcaaaa | 660 |
| tagagaaata taatgttccg ctgaacaggc ttaagatgat gtttgagaaa ggtgaaccaa | 720 |
| ctcaaactaa gattctccgg gcccaaagcc gaagtgcaag tggaaggaag atctctgaaa | 780 |
| acagctattc tctagatgac ctggaaatag gcccaggtca gttgtcatct tctacatttg | 840 |
| actcggagaa aaatgagagt agacgaaatc tggaacttcc acgcctctca gaaacctcta | 900 |
| taaaggatcg aatggccaag taccaggcag ctgcgtccaa acaaagcagc tcaaccaact | 960 |
| atacaaatga gctgaaagcc agtggtggcg aaatcaaaat tcataaaatg gagcaaaagg | 1020 |
| agaatgtgcc cccaggtcct gaggtctgca tcacccatca ggaaggggaa aagatttctg | 1080 |
| caaatgagaa tagcctggca gtccgttcca cccctgccga agatgactcc ccaggtgact | 1140 |
| cccaggttaa gagtgaggtt caacagcctg tccatcccaa gccactaagt ccagattcca | 1200 |
| gagcctccag tctttctgaa agttctcctc ccaaagcaat gaagaagttt caggcacctg | 1260 |
| caagagagac ctgcgtggaa tgtcagaaga cagtctatcc aatggagcgt ctcttggcca | 1320 |
| accagcaggt gtttcacatc agctgcttcc gttgctccta ttgcaacaac aaactcagtc | 1380 |
| taggaacata tgcatcttta catggaagaa tctattgtaa gcctcacttc aatcaactct | 1440 |
| ttaaatctaa gggcaactat gatgaaggct ttgggcacag accacacaag gatctatggg | 1500 |
| caagcaaaaa tgaaaacgaa gagattttgg agagaccagc ccagcttgca aatgcaaggg | 1560 |
| agaccctca cagcccaggg gtagaaaatg cccctattgc taaggtgggt gtcctggctg | 1620 |
| caagtatgga agccagggcc tcctctcagc aggagaagga agacaagcca gctgaaacca | 1680 |
| agaagctgag gatcgcctgg ccacccccca ctgaacttgg aagttcagga agtgccttgg | 1740 |
| aggaagggat caaaatgtca aagcccaaat ggcctcctga gacgaaatc agcaagcccg | 1800 |
| aagttcctga ggatgtcgat ctagatctga agaagctaag acgatcttct tcactgaagg | 1860 |
| aaagaagccg cccattcact gtagcagctt catttcaaag cacctctgtc aagagcccaa | 1920 |
| aaactgtgtc cccacctatc aggaaaggct ggagcatgtc agagcagaat gaagaatctg | 1980 |
| tgggtggaag agttgcagaa aggaaacaag tggaaaatgc caaggcttct aagaagaatg | 2040 |
| ggaatgtggg aaaaacaacc tggcaaaaca aagaatttaa aggagagaca gggaagagaa | 2100 |
| gtaaggaagg tcatagtttg gagatggaga atgaaatttt tgtagaaaat ggtgcagact | 2160 |
| ccgatgaaga tgataacagc ttcctcaaac aacatttcc acaagaaccc aagttttga | 2220 |
| attggtcgag ttttgtagac aacaccttg ctgaagaatt cactactcag aatcagaaat | 2280 |
| cccaggatgt ggaactttgg gagggagaag tggtcaaaga gctctctgtg aagaacaga | 2340 |
| taaagagaaa tcggtattat gatgaggatg aggatgaaga gtgacaaatt gcaatgatgc | 2400 |
| tgggccttaa attcatgtta gtgttagcga gccactgccc tttgtcaaaa tgtgatgcac | 2460 |
| ataagcaggt atcccagcat gaaatgtaat ttacttggaa gtaactttgg aaaagaattc | 2520 |
| cttcttaaaa tcaaaaacaa aacaaaaaaa cacaaaaaac acattctaaa tactagagat | 2580 |

-continued

```
aactttactt aaattcttca tcagtgatga tatgcataag tgctgtaagg cttgtaactg    2640
gggaaatatt ccacctgata atagcccaga ttctactgta ttcccaaaag gcaatattaa    2700
ggtagataga tgattagtag tatattgtta cacactattt tggaattaga gaacatacag    2760
aaggaattta ggggcttaaa cattacgact gaatgcactt agtataaagg gcacagtttg    2820 tatatttta aatgaatacc aatttaattt tttagtattt acctgttaag agattattta    2880
gtctttaaat tttttaggtt aattttcttg ctgtgatata tatgaggaat ttactacttt    2940
atgtcctgct ctctaaacta catcctgaac tcgacgtcct gaggtataac aacagagcac    3000
tttttgaggc aattgaaaaa ccaacctaca ctcttcggtg cttagagaga tctgctgtct    3060
cccaaataag cttttgtatc tgccagtgaa tttactgtac tccaaatgat tgctttcttt    3120
tctggtgata tctgtgcttc tcataattac tgaaagctgc aatatttag taataccttc    3180 gggatcactg tcccccatct tccgtgttag agcaaagtga agagtttaaa ggaggaagaa    3240
gaaagaactg tcttacacca cttgagctca gacctctaaa ccctgtattt cccttatgat    3300 gtccccttt tgagacacta attttttaaat acttactagc tctgaaatat attgattttt    3360
atcacagtat tctcagggtg aaattaaacc aactataggc cttttcttg ggatgatttt    3420 ctagtcttaa ggtttgggga cattataaac ttgagtacat ttgttgtaca cagttgatat    3480
tccaaattgt atggatggga gggagaggtg tcttaagctg taggcttttc tttgtactgc    3540
atttatagag atttagcttt aatatttttt agagatgtaa aacattctgc tttcttagtc    3600
ttacctagtc tgaaacattt ttattcaata aagattttaa ttaaaatttg             3650
```

<210> SEQ ID NO 4
<211> LENGTH: 759
<212> TYPE: PRT
<213> ORGANISM: Homo sapiens

<400> SEQUENCE: 4

```
Met Glu Ser Ser Pro Phe Asn Arg Arg Gln Trp Thr Ser Leu Ser Leu
 1               5                  10                  15

Arg Val Thr Ala Lys Glu Leu Ser Leu Val Asn Lys Asn Lys Ser Ser
            20                  25                  30

Ala Ile Val Glu Ile Phe Ser Lys Tyr Gln Lys Ala Ala Glu Glu Thr
        35                  40                  45

Asn Met Glu Lys Lys Arg Ser Asn Thr Glu Asn Leu Ser Gln His Phe
    50                  55                  60

Arg Lys Gly Thr Leu Thr Val Leu Lys Lys Trp Glu Asn Pro Gly
65                  70                  75                  80

Leu Gly Ala Glu Ser His Thr Asp Ser Leu Arg Asn Ser Ser Thr Glu
                85                  90                  95

Ile Arg His Arg Ala Asp His Pro Ala Glu Val Thr Ser His Ala
            100                 105                 110

Ala Ser Gly Ala Lys Ala Asp Gln Glu Glu Gln Ile His Pro Arg Ser
        115                 120                 125

Arg Leu Arg Ser Pro Pro Glu Ala Leu Val Gln Gly Arg Tyr Pro His
    130                 135                 140

Ile Lys Asp Gly Glu Asp Leu Lys Asp His Ser Thr Glu Ser Lys Lys
145                 150                 155                 160

Met Glu Asn Cys Leu Gly Glu Ser Arg His Glu Val Glu Lys Ser Glu
                165                 170                 175

Ile Ser Glu Asn Thr Asp Ala Ser Gly Lys Ile Glu Lys Tyr Asn Val
```

-continued

```
                180              185              190
Pro Leu Asn Arg Leu Lys Met Met Phe Glu Lys Gly Glu Pro Thr Gln
            195                 200                 205
Thr Lys Ile Leu Arg Ala Gln Ser Arg Ser Ala Ser Gly Arg Lys Ile
        210                 215                 220
Ser Glu Asn Ser Tyr Ser Leu Asp Asp Leu Glu Ile Gly Pro Gly Gln
225                 230                 235                 240
Leu Ser Ser Ser Thr Phe Asp Ser Glu Lys Asn Glu Ser Arg Arg Asn
                245                 250                 255
Leu Glu Leu Pro Arg Leu Ser Glu Thr Ser Ile Lys Asp Arg Met Ala
            260                 265                 270
Lys Tyr Gln Ala Ala Val Ser Lys Gln Ser Ser Thr Asn Tyr Thr
        275                 280                 285
Asn Glu Leu Lys Ala Ser Gly Gly Glu Ile Lys Ile His Lys Met Glu
        290                 295                 300
Gln Lys Glu Asn Val Pro Pro Gly Pro Glu Val Cys Ile Thr His Gln
305                 310                 315                 320
Glu Gly Glu Lys Ile Ser Ala Asn Glu Asn Ser Leu Ala Val Arg Ser
                325                 330                 335
Thr Pro Ala Glu Asp Asp Ser Arg Asp Ser Gln Val Lys Ser Glu Val
            340                 345                 350
Gln Gln Pro Val His Pro Lys Pro Leu Ser Pro Asp Ser Arg Ala Ser
        355                 360                 365
Ser Leu Ser Glu Ser Ser Pro Lys Ala Met Lys Lys Phe Gln Ala
        370                 375                 380
Pro Ala Arg Glu Thr Cys Val Glu Cys Gln Lys Thr Val Tyr Pro Met
385                 390                 395                 400
Glu Arg Leu Leu Ala Asn Gln Gln Val Phe His Ile Ser Cys Phe Arg
                405                 410                 415
Cys Ser Tyr Cys Asn Asn Lys Leu Ser Leu Gly Thr Tyr Ala Ser Leu
            420                 425                 430
His Gly Arg Ile Tyr Cys Lys Pro His Phe Asn Gln Leu Phe Lys Ser
        435                 440                 445
Lys Gly Asn Tyr Asp Glu Gly Phe Gly His Arg Pro His Lys Asp Leu
    450                 455                 460
Trp Ala Ser Lys Asn Glu Asn Glu Glu Ile Leu Glu Arg Pro Ala Gln
465                 470                 475                 480
Leu Ala Asn Ala Arg Glu Thr Pro His Ser Pro Gly Val Glu Asp Ala
                485                 490                 495
Pro Ile Ala Lys Val Gly Val Leu Ala Ala Ser Met Glu Ala Lys Ala
            500                 505                 510
Ser Ser Gln Gln Glu Lys Glu Asp Lys Pro Ala Glu Thr Lys Lys Leu
        515                 520                 525
Arg Ile Ala Trp Pro Pro Thr Glu Leu Gly Ser Ser Gly Ser Ala
        530                 535                 540
Leu Glu Glu Gly Ile Lys Met Ser Lys Pro Lys Trp Pro Pro Glu Asp
545                 550                 555                 560
Glu Ile Ser Lys Pro Glu Val Pro Glu Asp Val Asp Leu Asp Leu Lys
                565                 570                 575
Lys Leu Arg Arg Ser Ser Ser Leu Lys Glu Arg Ser Arg Pro Phe Thr
            580                 585                 590
Val Ala Ala Ser Phe Gln Ser Thr Ser Val Lys Ser Pro Lys Thr Val
        595                 600                 605
```

```
Ser Pro Pro Ile Arg Lys Gly Trp Ser Met Ser Glu Gln Ser Glu Glu
    610                 615                 620

Ser Val Gly Gly Arg Val Ala Glu Arg Lys Gln Val Glu Asn Ala Lys
625                 630                 635                 640

Ala Ser Lys Lys Asn Gly Asn Val Gly Lys Thr Thr Trp Gln Asn Lys
                645                 650                 655

Glu Ser Lys Gly Glu Thr Gly Lys Arg Ser Lys Glu Gly His Ser Leu
            660                 665                 670

Glu Met Glu Asn Glu Asn Ile Val Glu Asn Gly Ala Asp Ser Asp Glu
        675                 680                 685

Asp Asp Asn Ser Phe Leu Lys Gln Gln Ser Pro Gln Glu Pro Lys Ser
690                 695                 700

Leu Asn Trp Ser Ser Phe Val Asp Asn Thr Phe Ala Glu Glu Phe Thr
705                 710                 715                 720

Thr Gln Asn Gln Lys Ser Gln Asp Val Glu Leu Trp Glu Gly Glu Val
                725                 730                 735

Val Lys Glu Leu Ser Val Glu Glu Gln Ile Lys Arg Asn Arg Tyr Tyr
            740                 745                 750

Asp Glu Asp Glu Asp Glu Glu
        755

<210> SEQ ID NO 5
<211> LENGTH: 52
<212> TYPE: PRT
<213> ORGANISM: Homo sapiens

<400> SEQUENCE: 5

Cys Val Gly Cys Gln Lys Thr Val Tyr Pro Met Glu Arg Leu Leu Ala
1               5                   10                  15

Asn Gln Gln Val Phe His Ile Ser Cys Phe Arg Cys Ser Tyr Cys Asn
            20                  25                  30

Asn Lys Leu Ser Leu Gly Thr Tyr Ala Ser Leu His Gln Arg Ile Tyr
        35                  40                  45

Cys Lys Pro His
    50

<210> SEQ ID NO 6
<211> LENGTH: 54
<212> TYPE: PRT
<213> ORGANISM: Homo sapiens

<400> SEQUENCE: 6

Cys Tyr Phe Cys Lys Lys Arg Val Tyr Val Met Glu Arg Leu Ser Ala
1               5                   10                  15

Glu Gly His Phe Phe His Arg Glu Cys Phe Arg Cys Ser Ile Cys Ala
            20                  25                  30

Thr Thr Leu Arg Leu Ala Ala Tyr Thr Phe Asp Cys Asp Glu Gly Lys
        35                  40                  45

Phe Tyr Cys Lys Pro His
    50

<210> SEQ ID NO 7
<211> LENGTH: 52
<212> TYPE: PRT
<213> ORGANISM: Helianthus annuus

<400> SEQUENCE: 7
```

```
Cys Thr Val Cys Glu Lys Thr Val Tyr Leu Val Asp Lys Leu Val Ala
 1               5                  10                  15

Asn Gln Arg Val Tyr His Lys Ala Cys Phe Arg Cys His His Cys Asn
                20                  25                  30

Ser Thr Leu Lys Leu Ser Asn Phe Asn Ser Phe Asp Gly Val Val Tyr
            35                  40                  45

Cys Arg His His
    50
```

<210> SEQ ID NO 8
<211> LENGTH: 52
<212> TYPE: PRT
<213> ORGANISM: Homo sapiens

<400> SEQUENCE: 8

```
Cys Gly Ala Cys Glu Lys Thr Val Tyr His Ala Glu Glu Ile Gln Cys
 1               5                  10                  15

Asn Gly Arg Ser Phe His Lys Thr Cys Phe His Cys Met Ala Cys Arg
                20                  25                  30

Lys Ala Leu Asp Ser Thr Thr Val Ala Ala His Glu Ser Glu Ile Tyr
            35                  40                  45

Cys Lys Val Cys
    50
```

<210> SEQ ID NO 9
<211> LENGTH: 1803
<212> TYPE: DNA
<213> ORGANISM: Homo sapiens

<400> SEQUENCE: 9

| | | | | | |
|---|---|---|---|---|---|
| atggaaaatt | gtctaggaga | atccaggcat | gaagtagaaa | aatcagaaat | cagtgaaaac | 60 |
| acagatgctt | cgggcaaaat | agagaaatat | aatgttccgc | tgaacaggct | taagatgatg | 120 |
| tttgagaaag | gtgaaccaac | tcaaactaag | attctccggg | cccaaagccg | aagtgcaagt | 180 |
| ggaaggaaga | tctctgaaaa | cagctattct | ctagatgacc | tggaaatagg | cccaggtcag | 240 |
| ttgtcatctt | ctacatttga | ctcggagaaa | atgagagta | gacgaaatct | ggaacttcca | 300 |
| cgcctctcag | aaacctctat | aaaggatcga | atggccaagt | accaggcagc | tgcgtccaaa | 360 |
| caaagcagct | caaccaacta | tacaaatgag | ctgaaagcca | gtggtggcga | aatcaaaatt | 420 |
| cataaaatgg | agcaaaagga | gaatgtgccc | ccaggtcctg | aggtctgcat | cacccatcag | 480 |
| gaagggaaa | agatttctgc | aaatgagaat | agcctggcag | tccgttccac | ccctgccgaa | 540 |
| gatgactccc | caggtgactc | ccaggttaag | agtgaggttc | aacagcctgt | ccatcccaag | 600 |
| ccactaagtc | cagattccag | agcctccagt | ctttctgaaa | gttctcctcc | caaagcaatg | 660 |
| aagaagtttc | aggcacctgc | aagagagacc | tgcgtggaat | gtcagaagac | agtctatcca | 720 |
| atggagcgtc | tcttggccaa | ccagcaggtg | tttcacatca | gctgcttccg | ttgctcctat | 780 |
| tgcaacaaca | aactcagtct | aggaacatat | gcatctttac | atggaagaat | ctattgtaag | 840 |
| cctcacttca | atcaactctt | taaatctaag | ggcaactatg | atgaaggctt | tgggcacaga | 900 |
| ccacacaagg | atctatgggc | aagcaaaaat | gaaaacgaag | agattttgga | gagaccagcc | 960 |
| cagcttgcaa | atgcaaggga | gaccctcac | agcccagggg | tagaaaatgc | ccctattgct | 1020 |
| aaggtgggtg | tcctggctgc | aagtatggaa | gccagggcct | cctctcagca | ggagaaggaa | 1080 |
| gacaagccag | ctgaaaccaa | gaagctgagg | atcgcctggc | cacccccac | tgaacttgga | 1140 |
| agttcaggaa | gtgccttgga | ggaagggatc | aaaatgtcaa | agcccaaatg | gcctcctgaa | 1200 |

```
gacgaaatca gcaagcccga agttcctgag gatgtcgatc tagatctgaa gaagctaaga    1260
cgatcttctt cactgaagga aagaagccgc ccattcactg tagcagcttc atttcaaagc    1320
acctctgtca agagcccaaa aactgtgtcc ccacctatca ggaaaggctg gagcatgtca    1380
gagcagaatg aagaatctgt gggtggaaga gttgcagaaa ggaaacaagt ggaaaatgcc    1440
aaggcttcta agaagaatgg gaatgtggga aaaacaacct gcaaaacaa  agaatttaaa    1500 ggagagacag ggaagagaag taaggaaggt catagtttgg agatggagaa tgagaatttt    1560
gtagaaaatg gtgcagactc cgatgaagat gataacagct tcctcaaaca acaatttcca    1620
caagaaccca gttttttgaa ttggtcgagt tttgtagaca cacctttgc tgaagaattc     1680 actactcaga atcagaaatc ccaggatgtg aactttggg agggagaagt ggtcaaagag     1740
ctctctgtgg aagaacagat aaagagaaat cggtattatg atgaggatga ggatgaagag    1800
tga                                                                  1803

<210> SEQ ID NO 10
<211> LENGTH: 2283
<212> TYPE: DNA
<213> ORGANISM: Homo sapiens

<400> SEQUENCE: 10
atggaatcat ctccatttaa tagacggcaa tggacctcac tatcattgag ggtaacagcc      60
aaagaacttt ctcttgtcaa caagaacaag tcatcggcta ttgtggaaat attctccaag    120
taccagaaag cagctgaaga acaaacatg gagaagaaga gaagtaacac cgaaaatctc     180
tcccagcact ttagaaaggg gaccctgact gtgttaaaga agaagtggga gaacccaggg    240
ctgggagcag agtctcacac agactctcta cggaacagca gcactgagat taggcacaga    300
gcagaccatc ctcctgctga agtgacaagc cacgctgctt ctggagccaa agctgaccaa    360
gaagaacaaa tccacccag  atctagactc aggtcacctc ctgaagccct cgttcagggt    420
cgatatcccc acatcaagga cggtgaggat cttaaagacc actcaacaga agtaaaaaaa    480
atggaaaatt gtctaggaga atccaggcat gaagtagaaa aatcagaaat cagtgaaaac    540
acagatgctt cgggcaaaat agagaaatat aatgttccgc tgaacaggct taagatgatg    600
tttgagaaag gtgaaccaac tcaaactaag attctccggg cccaaagccg aagtgcaagt    660
ggaaggaaga tctctgaaaa cagctattct ctagatgacc tggaaatagg cccaggtcag    720
ttgtcatctt ctacatttga ctcggagaaa atgagagta  gacgaaatct ggaacttcca    780
cgcctctcag aaacctctat aaaggatcga atggccaagt accaggcagc tgcgtccaaa    840
caaagcagct caaccaacta tacaaatgag ctgaaagcca gtggtggcga aatcaaaatt    900
cataaaatgg agcaaaagga gaatgtgccc ccaggtcctg aggtctgcat cacccatcag    960 gaagggaaa  agatttctgc aaatgagaat agcctggcag tccgttccac ccctgccgaa   1020
gatgactccc caggtgactc ccaggttaag agtgaggttc aacagcctgt ccatcccaag   1080
ccactaagtc cagattccag agcctccagt ctttctgaaa gttctcctcc caaagcaatg   1140
aagaagtttc aggcacctgc aagagagacc tgcgtggaat gtcagaagac agtctatcca   1200
atggagcgtc tcttggccaa ccagcaggtg tttcacatca gctgcttccg ttgctcctat   1260
tgcaacaaca aactcagtct aggaacatat gcatctttac atggaagaat ctattgtaag   1320
cctcacttca atcaactctt taatctaagg gcaactatg  atgaaggctt tgggcacaga   1380
ccacacaagg atctatgggc aagcaaaaat gaaaacgaag agattttgga gagaccagcc   1440
```

-continued

```
cagcttgcaa atgcaaggga gacccctcac agcccagggg tagaaaatgc ccctattgct    1500
aaggtgggtg tcctggctgc aagtatggaa gccagggcct cctctcagca ggagaaggaa    1560
gacaagccag ctgaaaccaa gaagctgagg atcgcctggc caccccccac tgaacttgga    1620
agttcaggaa gtgccttgga ggaagggatc aaaatgtcaa agcccaaatg gcctcctgaa    1680
gacgaaatca gcaagcccga agttcctgag gatgtcgatc tagatctgaa gaagctaaga    1740
cgatcttctt cactgaagga aagaagccgc ccattcactg tagcagcttc atttcaaagc    1800
acctctgtca agagcccaaa aactgtgtcc ccacctatca ggaaaggctg gagcatgtca    1860
gagcagaatg aagaatctgt gggtggaaga gttgcagaaa ggaaacaagt ggaaaatgcc    1920
aaggcttcta agaagaatgg gaatgtggga aaaacaacct ggcaaaacaa agaatttaaa    1980
ggagagacag ggaagagaag taaggaaggt catagtttgg agatggagaa tgagaatttt    2040
gtagaaaatg gtgcagactc cgatgaagat gataacagct tcctcaaaca acaatttcca    2100
caagaaccca agttttttgaa ttggtcgagt tttgtagaca acacctttgc tgaagaattc    2160
actactcaga atcagaaatc ccaggatgtg gaactttggg agggagaagt ggtcaaagag    2220
ctctctgtgg aagaacagat aaagagaaat cggtattatg atgaggatga ggatgaagag    2280
tga                                                                  2283
```

EPITHELIAL PROTEIN LOST IN NEOPLASM (EPLIN)

CROSS REFERENCE TO RELATED APPLICATIONS

This application claims priority from U.S. Provisional Application Serial No. 60/153,024, filed Sep. 8, 1999, the disclosure of which is incorporated herein by reference.

FIELD OF THE INVENTION

This invention relates generally to gene expression in normal and neoplastic cells, and specifically to a novel tumor suppressor gene, EPLIN (epithelial protein lost in neoplasm), and its gene products.

BACKGROUND OF THE INVENTION

Progression of cancer in humans is associated with accumulation of genetic mutations. Most genes mutated in cancer are involved primarily in the maintenance of genomic integrity (Lengauer et al., Nature, 396:643, 1998) and the control of cell cycle progression (Sherr, Genes and Devel., 12:2984, 1998). These mutations in turn affect expression of a larger number of cellular genes which collectively are responsible for the changes in cell phenotype. Some of the differentially expressed genes function as oncogenes, while others behave as tumor suppressors to facilitate the development or progression of cancer (Weinberg, Annals of the New York Acad of Sci., 758:331, 1995). As the number of genes that are differentially expressed in cancer far exceed the number of mutated genes, they provide an abundant source of targets that can be exploited to dissect the complex changes that underlie cellular transformation.

Cancer genes are broadly classified into "oncogenes" which, when activated, promote tumorigenesis, and "tumor suppressor genes" which, when nonfunctional, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

Oncogenes are somatic cell genes that are mutated from their wild-type alleles (the art refers to these wild-type alleles as protooncogenes) into forms which are able to induce tumorigenesis under certain conditions. There is presently a substantial literature on known and putative oncogenes and the various alleles of these oncogenes.

Tumor suppressor genes are genes that, in their wild-type alleles, express proteins that suppress abnormal cellular proliferation. When the gene coding for a tumor suppressor protein is mutated, deleted or transcriptionally nonfunctional, the resulting absence of wild-type tumor suppressor protein expression promotes abnormal cellular proliferation. A number of well-studied human tumors and tumor cell lines have been shown to have missing or nonfunctional tumor suppressor genes. Examples of tumor suppression genes include, but are not limited to, the retinoblastoma susceptibility gene or RB gene, the p53 gene, the deleted in colon carcinoma (DCC) gene and the neurofibromatosis type 1 (NF-1) tumor suppressor gene (Weinberg, R. A. Science, 1991, 254:1138). Loss of function or inactivation of tumor suppressor genes may play a central role in the initiation and/or progression of a significant number of human cancers.

The present invention shows that many cancers exhibit decreased EPLIN expression relative to their tissues of origin. The limitation and failings of the prior art to provide meaningful markers which correlate with the presence of cell proliferative disorders, such as cancer, has created a need for markers which can be used diagnostically, prognostically, and therapeutically over the course of such disorders. The present invention fulfills such a need.

SUMMARY OF THE INVENTION

The present invention is based on the seminal discovery of a novel tumor suppressor gene, EPLIN (epithelial protein lost in neoplasm), the expression of which is altered in multiple common human tumor types. The invention provides EPLIN polypeptides (SEQ ID NO:2 and SEQ ID NO:4) as well as polynucleotide sequences encoding the polypeptides (SEQ ID NO:1 or SEQ ID NO:9 and SEQ ID NO:3 or SEQ ID NO:10) and antibodies which bind to the polypeptides set forth in SEQ ID NO:2 and SEQ ID NO:4. Thus, it is an object of the present invention to provide a substantially purified EPLIN polypeptide and nucleic acid encoding the EPLIN polypeptide. In accordance with another aspect of the invention, an expression vector containing EPLIN nucleic acid is provided. Also included is a method for producing the EPLIN polypeptides and antibodies which bind to the EPLIN polypeptides.

In yet another aspect, the invention provides a method for identifying a compound which binds to EPLIN polypeptide that includes incubating components comprising the compound and EPLIN polypeptide under conditions sufficient to allow the components to interact and measuring the binding of the compound to EPLIN polypeptide.

In another aspect, the present invention provides a method of detecting a neoplastic cell in a sample by contacting a sample suspected of containing a neoplastic cell with a reagent that binds to an EPLIN-specific cell component and detecting binding of the reagent to the component.

In another aspect, the invention provides a method of detecting a cell proliferative disorder in a sample from a subject by contacting a first sample having, or suspected of having, a cell proliferative disorder with a reagent that binds to an EPLIN-specific cell component and detecting binding of the reagent to the component; contacting a second cell not having a cell proliferative disorder with a reagent that binds to an EPLIN-specific cell component and detecting binding of the reagent to the component; comparing the level of binding in the first sample with the level of binding in the second sample, wherein a decreased level of binding of the reagent to an EPLIN-specific cell component from the first sample is indicative of a cell proliferative disorder.

A kit useful for the detection of an EPLIN-specific cell component, the kit comprising carrier means containing one or more containers comprising a first container containing an EPLIN-specific binding reagent.

In yet another aspect, the present invention provides a method of ameliorating a cell proliferative disorder associated with EPLIN, comprising administering to a subject with the disorder, a therapeutically effective amount of reagent which regulates EPLIN activity.

In a further aspect, the invention provides a method of gene therapy comprising introducing into cells of a host subject, an expression vector comprising a nucleotide sequence encoding EPLIN, in operable linkage with a promoter.

Other objects, features and advantages of the present invention will become apparent from the following detailed description. It should be understood, however, that the detailed description and the specific examples, while indi-

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1C shows the alignment of the EPLIN LIM domain sequence (amino acid residues 390–441 of SEQ ID NO:4) with the LIM domain of the mutant SREBP-2 (SEQ ID NO:5), KIAA0750 (SEQ ID NO:6), plant transcription factor SF3 (SEQ ID NO:7), and muscle LIM protein (SEQ ID NO:8).

DETAILED DESCRIPTION

Figure 1A:
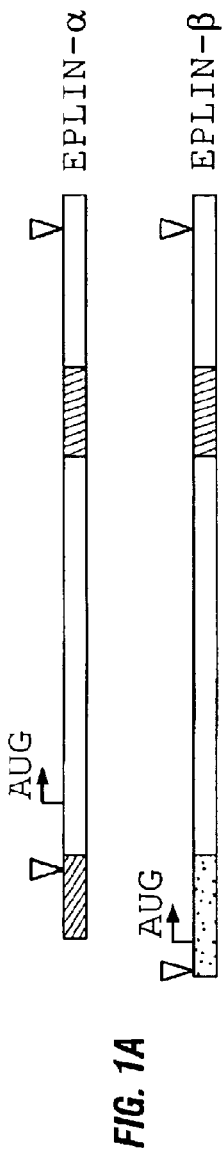
FIG. 1A shows a schematic diagram of two EPLIN cDNAs. The sequence of two isoforms diverge at the 5' end (indicated by the stripped and dotted boxes).

Various genes are differentially expressed in human cancers. The present invention provides the novel tumor suppressor gene EPLIN (epithelial protein lost in neoplasm) encoding novel cytoskelet al proteins preferentially expressed in human epithelial cells. Two EPLIN isoforms, a 600 amino acid EPLIN-α (SEQ ID NO:2) and a 759 amino acid EPLIN-β (SEQ ID NO:4), are detected in primary epithelial cells of oral mucosa, prostate and mammary glands. Both EPLIN isoforms localize to filamentous actin and suppress cell proliferation when overexpressed. Thus, the invention further provides a polynucleotide (SEQ ID NO:1 or SEQ ID NO:9) encoding the amino acid sequence for EPLIN-α and a polynucleotide (SEQ ID NO:3 or SEQ ID NO:10) encoding the amino acid sequence for EPLIN-β. These findings indicate that the loss of EPLIN seen in cancer cells may play a role in cancer progression. Based on this discovery, it is an object of the invention to provide compounds, and pharmaceutical compositions thereof, which modulate cell proliferation.

The EPLIN protein, fragments thereof, and derivatives and other variants of the sequence in SEQ ID NO:2 or SEQ ID NO:4 thereof are collectively referred to as "polypeptides or proteins of the invention" or "EPLIN polypeptides or proteins." Nucleic acid molecules encoding such polypeptides or proteins are collectively referred to as "nucleic acids of the invention" or "EPLIN nucleic acids." EPLIN molecules refer to EPLIN nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with respect to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequence naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in Current Protocols in Molecular Biology, John Wiley & Sons, N.Y. (1989), 6.3.1–6.3.6. Aqueous and nonaqueous methods are described in that reference and either can be used. A preferred example of stringent hybridization conditions includes hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a sequence is within the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NOs:1 or 3, corresponds to a naturally occurring nucleic acid molecule.

As used herein, a "naturally occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules that include an open reading frame encoding an EPLIN protein, preferably a mammalian EPLIN protein, and further can include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of EPLIN protein having less than about 30%, 20%, 10% and more preferably 5% (by dry weight), of non-EPLIN protein (also referred to herein as a "contaminating protein"), or of chemical precursors or non-EPLIN chemicals. When the EPLIN protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of EPLIN (e.g., the sequence of SEQ ID NO:2 or 4) without abolishing or more preferably, without substantially altering a biological activity of the EPLIN protein, whereas an "essential" amino acid residue results in such a change. For example, amino acid residues that are conserved among the polypeptides of the present invention are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., asoartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an EPLIN protein is preferably replaced with another amino acid residue from the same side chain family. Alternatively, in another embodiment, mutations can be introduced randomly along all or part of an EPLIN coding sequence, such as by saturation mutagenesis, and the resultant mutants can be screened for EPLIN biological activity to identify mutants that retain activity. Following mutagenesis of SEQ ID NO:1 or 3, the encoded protein can be expressed recombinantly and the activity of the protein can be determined.

As used herein, a "biologically active portion" of an EPLIN protein includes a fragment of an EPLIN protein that participates in an interaction between an EPLIN molecule and a non-EPLIN molecule. Biologically active portions of an EPLIN protein include peptides comprising amino acid sequences sufficiently homologous to or derived from the amino acid sequence of the EPLIN protein, e.g., the amino acid sequence shown in SEQ ID NO:2, which include less amino acids than the full length EPLIN protein and exhibit at least one activity of an EPLIN protein, such as tumor suppressor activity. Typically, biologically active portions comprise a domain or motif with at least one activity of the EPLIN protein. A biologically active portion of an EPLIN protein can be a polypeptide that is, for example, 10, 25, 50, 100, 200, 300 or more amino acids in length. Biologically active portions of an EPLIN protein can be used as targets for developing agents that modulate an EPLIN mediated activity.

Calculations of homology or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.*, 48:444–453) algorithm which has been incorporated into the GAP program in the GCG software package (available on the world-wide web at gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world-wide web at gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.*, 215:403–10. BLAST nucleotide searches can be performed with the NBLAST program, score=100, wordlength=12 to obtain nucleotide sequences homologous to EPLIN nucleic acid molecules of the invention. BLAST protein searches can be performed with the XBLAST program, score=50, wordlength=3 to obtain amino acid sequences homologous to EPLIN protein molecules of the invention. To obtain gapped alignments for comparison purposes, Gapped BLAST can be utilized as described in Altschul et al., (1997) *Nucleic Acids Res.*, 25(17):3389–3402. When utilizing BLAST and Gapped BLAST programs, the default parameters of the respective programs (e.g., XBLAST and NBLAST) can be used. See world-wide web at ncbi.nlm.nih.gov.

"Misexpression or aberrant expression," as used herein, refers to a non-wild type pattern of gene expression at the RNA or protein level. It includes: expression at non-wild type levels, i.e., over or underexpression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, can refer to a mammal, e.g., a human, or to an experimental animal or disease model. The subject also can be a non-human animal, e.g., a horse, cow, goat, or other domestic animal.

Thus, in a first embodiment, the present invention provides substantially pure EPLIN polypeptides consisting essentially of the amino acid sequence of SEQ ID NO:2 and SEQ ID NO:4. The term "substantially pure" as used herein refers to EPLIN polypeptide that is substantially free of other proteins, lipids, carbohydrates or other materials with which it is naturally associated. One skilled in the art can purify EPLIN using standard techniques for protein purification. The substantially pure polypeptide will yield a single major band on a non-reducing polyacrylamide gel. The purity of an EPLIN polypeptide can also be determined by amino-terminal amino acid sequence analysis.

The invention includes functional polypeptides of EPLIN-α and EPLIN-β, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. Functional fragments of the EPLIN polypeptide, includes fragments of EPLIN as long as the activity, e.g., tumor suppressor activity, of EPLIN remains. Smaller peptides containing the biological activity of EPLIN are included in the invention. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide that encodes a functional polypeptide as described herein.

As previously noted, minor modifications of the EPLIN primary amino acid sequence may result in proteins that have substantially equivalent activity as compared to the EPLIN polypeptide described herein. Such modifications may be deliberate, as by site-directed mutagenesis, or may be spontaneous. All of the polypeptides produced by these modifications are included herein as long as the tumor suppressor activity of EPLIN is present. Further, deletion of one or more amino acids can also result in a modification of the structure of the resultant molecule without significantly altering its activity. This can lead to the development of a smaller active molecule that would have broader utility. For example, it is possible to remove amino or carboxy terminal amino acids that may not be required for EPLIN activity.

The invention also provides an isolated polynucleotide sequence consisting essentially of a polynucleotide sequence encoding a polypeptide having the amino acid sequence of SEQ ID NO:2 or SEQ ID NO:4. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences that encode EPLIN. It is understood that all polynucleotides encoding all or a portion of EPLIN are also included herein, as long as they encode a polypeptide with EPLIN activity. Such polynucleotides include naturally occurring, synthetic, and intentionally manipulated polynucleotides. For example, EPLIN polynucleotide may be subjected to site-directed mutagenesis. The polynucleotide sequence for EPLIN also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of EPLIN polypeptide encoded by the nucleotide sequence is functionally unchanged. In addition, the invention also includes a polynucleotide consisting essentially of a polynucleotide sequence encoding a polypeptide having an amino acid sequence of SEQ ID NO:2 or SEQ ID NO:4 and having at least one epitope for an antibody immunoreactive with EPLIN polypeptide.

The invention further encompasses nucleic acid molecules that differ from the nucleotide sequence shown in SEQ ID NO:1 or 3. Such differences can be due to degeneracy of the genetic code (and result in a nucleic acid that encodes the same EPLIN proteins as those encoded by the nucleotide sequence disclosed herein. In another embodiment, an isolated nucleic acid molecule of the invention has a nucleotide sequence encoding a protein having an amino acid sequence that differs by at least 1, but less than 5, 10, 20, 50, or 100 amino acid residues than that shown in SEQ ID NO:2 or 4. If alignment is needed for this comparison the sequences should be aligned for maximum homology. "Looped" out sequences from deletions, insertions, or mismatches, are considered differences.

Nucleic acids of the invention can be chosen for having codons, which are preferred or non-preferred, for a particular expression system. E.g., the nucleic acid can be one in which at least one codon, at preferably at least 10%, or 20% of the codons has been altered such that the sequence is optimized for expression in *E. coli*, yeast, human, insect, or chinese hamster ovary (CHO) cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared with the encoded product).

In a preferred embodiment, the nucleic acid differs from that of SEQ ID NO:1 or 3 as follows: by at least one but less than 10, 20, 30, or 40 nucleotides; at least one but less than 1%, 5%, 10% or 20% of the nucleotides in the subject nucleic acid. If necessary for this analysis, the sequences should be aligned for maximum homology. "Looped" out sequences from deletions, insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or a fragment of this sequence. Such nucleic acid molecules can readily be identified as being able to hybridize under stringent conditions, to the nucleotide sequence shown in SEQ ID NO 1 or a fragment of the sequence. Nucleic acid molecules corresponding to orthologs, homologs, and allelic variants of the EPLIN cDNAs of the invention can further be isolated by mapping to the same chromosome or locus as the EPLIN gene. Preferred variants include those that are correlated with a tumor suppressor activity.

Allelic variants of EPLIN, e.g., human EPLIN, include both functional and non-functional proteins. Functional allelic variants are naturally occurring amino acid sequence variants of the EPLIN protein within a population that maintain the ability to function as a tumor suppressor protein. Functional allelic variants typically will contain only conservative substitution of one or more amino acids of SEQ ID NO:2 or 4, or substitution, deletion or insertion of non-critical residues in non-critical regions of the protein. Non-functional allelic variants are naturally occurring amino acid sequence variants of the EPLIN, e.g., human EPLIN. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Polynucleotides encoding EPLIN include the nucleotide sequence of SEQ ID NO:1 or SEQ ID NO: 9 and SEQ ID NO:3 or SEQ ID NO:10, as well as nucleic acid sequences complementary to those sequences sequence. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the polypeptide of SEQ ID NO:2 or SEQ ID NO:4 under physiological conditions.

In another aspect, the invention features, an isolated nucleic acid molecule that is antisense to EPLIN. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire EPLIN coding strand, or to only a portion thereof (e.g., the coding region of EPLIN corresponding to SEQ ID NO:3). In another embodiment, the antisense nucleic acid molecule is antisense to a "noncoding region" of the coding strand of a nucleotide sequence encoding EPLIN (e.g., the 5' and 3' untranslated regions).

An antisense nucleic acid can be designed such that it is complementary to the entire coding region of EPLIN mRNA, but more preferably is an oligonucleotide that is antisense to only a portion of the coding or noncoding region of EPLIN mRNA. For example, the antisense oligonucleotide can be complementary to the region surrounding the translation start site of EPLIN mRNA, e.g., between the −10 and +10 regions of the target gene nucleotide sequence. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions with procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding an EPLIN protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong polymerase II or polymerase III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual b-units, the strands run parallel to each other (Gaultier et al. (1987) *Nucleic Acids. Res.*, 15:6625–6641). The antisense nucleic acid molecule can also comprise a 2'-o-methylribonucleotide (Inoue et al. (1987) *Nucleic Acids Res.*, 15:6131–6148) or a chimeric RNA-DNA analogue (Inoue et al. (1987) *FEBS Lett.*, 215:327–330).

In still another embodiment, an antisense nucleic acid of the invention is a ribozyme. A ribozyme having specificity for an EPLIN-encoding nucleic acid can include one or more sequences complementary to the nucleotide sequence of an EPLIN cDNA disclosed herein (i.e., SEQ ID NO:1 or 3), and a sequence having known catalytic sequence responsible for mRNA cleavage (see U.S. Pat. No. 5,093,246 or Haselhoff and Gerlach (1988) *Nature*, 334:585–591). For example, a derivative of a Tetrahymena L-19 IVS RNA can be constructed in which the nucleotide sequence of the active site is complementary to the nucleotide sequence to be cleaved in an EPLIN-encoding mRNA. See, e.g., Cech et al. U.S. Pat. No. 4,987,071; and Cech et al. U.S. Pat. No. 5,116,742. Alternatively, EPLIN mRNA can be used to select a catalytic RNA having a specific ribonuclease activity from a pool of RNA molecules. See, e.g., Bartel, D. and Szostak, J. W. (1993) *Science*, 261:1411–1418.

EPLIN gene expression can be inhibited by targeting nucleotide sequences complementary to the regulatory region of the EPLIN (e.g., the EPLIN promoter and/or enhancers) to form triple helical structures that prevent transcription of the EPLIN gene in target cells. See, generally, Helene, C. (1991) *Anticancer Drug Des.*, 6(6):569–84; Helene, C. et al. (1992) Ann. N.Y. Acad. Sci., 660:27–36; and Maher, L. J. (1992) *Bioassays*, 14(12):807–15. The potential sequences that can be targeted for triple helix formation can be increased by creating a "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

DNA sequences of the invention can be obtained by several methods. For example, the DNA can be isolated using hybridization techniques that are well known in the art. These include, but are not limited to: (1) hybridization of genomic or cDNA libraries with probes to detect homologous nucleotide sequences and (2) antibody screening of expression libraries to detect cloned DNA fragments with shared structural features.

Preferably the EPLIN polynucleotide of the invention is derived from a mammalian organism, and most preferably from humnan. Screening procedures that rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture that is its complete complement (Wallace et al., *Nucl. Acid Res.*, 9:879, 1981).

The development of specific DNA sequences encoding EPLIN can also be obtained by: (1) isolation of double-stranded DNA sequences from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries that are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.*, 11:2325, 1983).

A cDNA expression library, such as lambda gt11, can be screened indirectly for EPLIN peptides having at least one epitope, using antibodies specific for EPLIN. Such antibodies can be either polyclonally or monoclonally derived and used to detect expression product indicative of the presence of EPLIN cDNA.

DNA sequences encoding EPLIN can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the EPLIN polynucleotide sequences may be inserted into a recombinant expression vector. The term "recombinant expression vector" refers to a plasmid, virus or other vehicle known in the art that has been manipulated by insertion or incorporation of the EPLIN genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding EPLIN can be expressed in either prokaryotes or eukaryotes. Hosts can include microbial, yeast, insect, and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

In another aspect, the invention provides EPLIN chimeric or fusion proteins. As used herein, an EPLIN "chimeric protein" or "fusion protein" includes an EPLIN polypeptide linked to a non-EPLIN polypeptide. A "non-EPLIN polypeptide" refers to a polypeptide having an amino acid sequence corresponding to a protein that is not substantially homologous to the EPLIN protein, e.g., a protein that is different from the EPLIN protein and that is derived from the same or a different organism. The EPLIN polypeptide of the fusion protein can correspond to all or a portion e.g., a fragment described herein of an EPLIN amino acid sequence. In a preferred embodiment, an EPLIN fusion protein includes at least one (e.g. two) biologically active portion of an EPLIN protein. The non-EPLIN polypeptide can be fused to the N-terminus or C-terminus of an EPLIN polypeptide.

The fusion protein can include a moiety that has high affinity for a ligand. For example, the fusion protein can be a GST-EPLIN fusion protein in which the EPLIN sequences are fused to the C-terminus of the GST sequences. Such fusion proteins can facilitate the purification of recombinant EPLIN. Alternatively, the fusion protein can be an EPLIN protein containing a heterologous signal sequence at its N-terminus. In certain host cells (e.g., mammalian host cells), expression and/or secretion of EPLIN can be increased through use of a heterologous signal sequence.

Fusion proteins can include all or a part of a serum protein, e.g., an IgG constant region, or human serum albumin.

The EPLIN fusion proteins of the invention can be incorporated into pharmaceutical compositions and administered to a subject in vivo. The EPLIN fusion proteins can be used to affect the bioavailability of an EPLIN substrate. EPLIN fusion proteins may be useful therapeutically for the treatment of disorders caused by, for example: (i) aberrant modification or mutation of a gene encoding an EPLIN protein; (ii) mis-regulation of the EPLIN gene; and (iii) aberrant post-translational modification of an EPLIN protein.

Moreover, EPLIN-fusion proteins of the invention can be used as immunogens to produce anti-EPLIN antibodies in a subject, to purify EPLIN ligands, and in screening assays to identify molecules that inhibit the interaction of EPLIN with an EPLIN substrate.

Expression vectors are commercially available that already encode a fusion moiety (e.g., a GST polypeptide). An EPLIN-encoding nucleic acid can be cloned into such an expression vector such that the fusion moiety is linked in-frame to the EPLIN protein.

In another aspect, the invention features a variant of an EPLIN polypeptide, e.g., a polypeptide that functions as an agonist (mimetic) or as an antagonist of EPLIN activities. Variants of the EPLIN proteins can be generated by mutagenesis, e.g., discrete point mutations, the insertion or deletion of sequences or the truncation of an EPLIN protein. An agonist of the EPLIN protein retains substantially the same, or a subset, of the biological activities of the naturally occurring form of an EPLIN protein. An antagonist of an EPLIN protein can inhibit one or more of the activities of the naturally occurring form of the EPLIN protein by, for example, competitively modulating an EPLIN-mediated activity of an EPLIN protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the EPLIN protein.

Variants of an EPLIN protein can be identified by screening combinatorial libraries of mutants, e.g., truncation mutants, of an EPLIN protein for agonist or antagonist activity.

Libraries of fragments e.g., N terminal, C terminal, or internal fragments, of an EPLIN protein coding sequence can be used to generate a variegated population of fragments for screening and subsequent selection of variants of an EPLIN protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property are known. Recursive ensemble mutagenesis (REM), a new technique which enhances the frequency of functional mutants in the libraries, can be used in combination with screening assays to identify EPLIN variants (Arkin and Yourvan (1992) Proc. Natl. Acad. Sci. USA, 89:7811–7815; Delgrave et al. (1993) Protein Engineering, 6(3):327–331).

Cell based assays can be exploited to analyze a variegated EPLIN library. For example, a library of expression vectors can be transfected into a cell line, e.g., a cell line, which ordinarily responds to EPLIN in a substrate-dependent manner. The transfected cells are then contacted with EPLIN and the effect of the expression of the mutant on signaling by the EPLIN substrate can be detected, e.g., by measuring tumor suppressor activity in an appropriate assay. Plasmid DNA can then be recovered from the cells that score for inhibition, or alternatively, potentiation of signaling by the EPLIN substrate, and the individual clones further characterized.

In another aspect, the invention features a method of making an EPLIN polypeptide, e.g., a peptide having a non-wild type activity, e.g., an antagonist, agonist, or super agonist of a naturally occurring EPLIN polypeptide, e.g., a naturally occurring EPLIN polypeptide. The method includes: altering the sequence of an EPLIN polypeptide, e.g., by substitution or deletion of one or more residues of a non-conserved region, a domain, or residue disclosed herein, and testing the altered polypeptide for the desired activity.

In another aspect, the invention features a method of making a fragment or analog of an EPLIN polypeptide that retains at least one biological activity of a naturally occurring EPLIN polypeptide. The method includes: altering the sequence, e.g., by substitution or deletion of one or more residues, of an EPLIN polypeptide, e.g., altering the sequence of a non-conserved region, or a domain or residue described herein, and testing the altered polypeptide for the desired activity.

Screening Method

EPLIN nucleic acids, proteins, and derivatives of the present invention also have uses in screening assays to detect molecules that specifically bind to EPLIN nucleic acids, proteins, or derivatives and thus have potential use as agonists or antagonists of EPLIN, in particular, molecules that affect cell proliferation. In one embodiment, such assays are performed to screen for molecules with potential utility as anti-cancer drugs or lead compounds for drug development. The invention provides assays to detect molecules that specifically bind to EPLIN nucleic acids, proteins, or derivatives. For example, recombinant cells expressing EPLIN nucleic acids can be used to recombinantly produce EPLIN proteins in these assays, to screen for molecules that bind to an EPLIN protein. Molecules (e.g., putative binding partners of EPLIN) are contacted with the EPLIN protein (or fragment thereof) under conditions conducive to binding, and then molecules that specifically bind to the EPLIN protein are identified. Similar methods can be used to screen for molecules that bind to EPLIN derivatives or nucleic acids. Methods that can be used to carry out the foregoing are commonly known in the art.

By way of example, diversity libraries, such as random or combinatorial peptide or nonpeptide libraries can be screened for molecules that specifically bind to EPLIN. Many libraries are known in the art that can be used, e.g., chemically synthesized libraries, recombinant (e.g., phage display libraries), and in vitro translation-based libraries.

For example, agonists and antagonists of EPLIN can be identified using "biochip" technology. "Biochips" or arrays of binding agents, such as oligonucleotides and peptides, have become an increasingly important tool in the biotechnology industry and related fields.

These binding agent arrays, in which a plurality of binding agents are deposited onto a solid support surface in the form of an array or pattern, find use in a variety of applications, including drug screening, nucleic acid sequencing, mutation analysis, and the like. One important use of biochips is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared.

In methods of differential gene expression, arrays find use by serving as a substrate to which is bound polynucleotide "probe" fragments. One then obtains "targets" from analogous cells, tissues, or organs of a healthy and diseased organism. The targets are then hybridized to the immobilized set of polynucleotide "probe" fragments. Differences between the resultant hybridization patterns are then detected and related to differences in gene expression in the two sources. Thus, the present invention provides nucleic acid and amino acid sequences useful for screening for differential expression of EPLIN in a cell.

The invention includes antibodies immunoreactive with EPLIN polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler et al., *Nature*, 256:495, 1975). The term antibody as used in this invention is meant to include intact molecules as well as fragments thereof, such as Fab and $F(ab')_2$, which are capable of binding an epitopic determinant on EPLIN.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Diagnostic Uses of EPLIN

EPLIN proteins, analogues, derivatives, and subsequences thereof, EPLIN nucleic acids (and sequences complementary thereto), anti-EPLIN antibodies, have uses in diagnostics. Such molecules can be used in assays, such as immunoassays, to detect, prognose, diagnose, or monitor various conditions, diseases, and disorders affecting EPLIN expression, or monitor the treatment thereof. In particular, such an immunoassay is carried out by a method comprising contacting a sample derived from a patient with an anti-EPLIN antibody under conditions such that immunospecific binding can occur, and detecting or measuring the amount of any immunospecific binding by the antibody. In a specific aspect, such binding of antibody, in tissue sections, can be used to detect aberrant EPLIN localization or aberrant (e.g., low or absent) levels of EPLIN. In a specific embodiment, antibody to EPLIN can be used to assay in a patient tissue or serum sample for the presence of EPLIN where an aberrant level of EPLIN is an indication of a diseased condition. By "aberrant levels," is meant increased or decreased levels relative to that present, or a standard level representing that present, in an analogous sample from a portion of the body or from a subject not having the disorder.

Thus, the invention provides a method of detecting a cell proliferative disorder in a sample from a subject by contacting a first sample having, or suspected of having, a cell proliferative disorder with a reagent that binds to an EPLIN-specific cell component and detecting binding of the reagent to the component; contacting a second cell not having a cell proliferative disorder with a reagent that binds to an EPLIN-specific cell component and detecting binding of the reagent to the component; comparing the level of binding in the first sample with the level of binding in the second sample, wherein a decreased level of binding of the reagent to an EPLIN-specific cell component from the first sample is indicative of a cell proliferative disorder.

The term "cell proliferative disorder," as used herein, refers to a condition characterized by abnormal cell growth. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tamorigenic or malignant cells, but also can include normal cells. As used herein, an "EPLIN-specific cell component" includes, but is not limited to, RNA and DNA encoding an EPLIN protein, the EPLIN protein and fragments thereof, and EPLIN variants including translocations in EPLIN nucleic acids, truncations in the EPLIN gene or protein, changes in nucleotide or amino acid sequence relative to wild-type EPLIN.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

EPLIN genes and related nucleic acid sequences and subsequences, including complementary sequences, can also be used in hybridization assays. EPLIN nucleic acid sequences, or subsequences thereof comprising about at least 8 nucleotides, can be used as hybridization probes.

Hybridization assays can be used to detect, prognose, diagnose, or monitor conditions, disorders, or disease states associated with aberrant changes in EPLIN expression and/ or activity as described. In particular, such a hybridization assay is carried out by a method comprising contacting a sample containing nucleic acid with a nucleic acid probe capable of hybridizing to EPLIN DNA or RNA, under conditions such that hybridization can occur, and detecting or measuring any resulting hybridization.

In specific embodiments, diseases and disorders involving over-proliferation of cells can be diagnosed, or their suspected presence can be screened for, or a predisposition to develop such disorders can be detected, by detecting increased levels of EPLIN protein, EPLIN RNA, or EPLIN functional activity or by detecting mutations in EPLIN RNA, DNA or protein (e.g., translocations in EPLIN nucleic acids, truncations in the EPLIN gene or protein, changes in nucleotide or amino acid sequence relative to wild-type EPLIN) that cause increased expression or activity of EPLIN. By way of example, levels of EPLIN protein can be detected by immunoassay, levels of EPLIN RNA can be detected by hybridization assays (e.g., Northern blots, dot blots), translocations and point mutations in EPLIN nucleic acids can be detected by Southern blotting, RFLP analysis, PCR using primers that preferably generate a fragment spanning at least most of the EPLIN gene, sequencing of the EPLIN genomic DNA or cDNA obtained from the patient.

In a preferred embodiment, levels of EPLIN mRNA or protein in a patient sample are detected or measured, in which increased levels indicate that the subject has, or has a predisposition to developing, a malignancy or hyperproliferative disorder; in which the increased levels are relative to the levels present in an analogous sample from a portion of the body or from a subject not having the malignancy or hyperproliferative disorder, as the case may be.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting decreased levels of EPLIN protein, EPLIN RNA, or EPLIN functional activity, or by detecting mutations in EPLIN RNA, DNA or protein (e.g., translocations in EPLIN nucleic acids, truncations in the gene or protein, changes in nucleotide or amino acid sequence relative to wild-type EPLIN) that cause decreased expression or activity of EPLIN. By way of example, levels of EPLIN protein, levels of EPLIN RNA, EPLIN binding activity, and the presence of translocations or point mutations can be determined as described.

In a specific embodiment, levels of EPLIN mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the EPLIN antigen for which the monoclonal antibodies are specific. The concentration of detectably labeled monoclonal antibody which is administered should be sufficient such that the binding to those cells having EPLIN is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin, either directly or indirectly, by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

Kits for Detection of EPLIN

The materials for use in the method of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise an EPLIN or EPLIN binding reagent, such as an antibody or nucleic acid, respectively. The constituents may be present in liquid or lyophilized form, as desired. Thus, the present invention also provides a kit useful for the detection of an EPLIN-specific cell component, the kit comprising carrier means containing one or more containers comprising a first container containing an EPLIN-specific binding reagent. As used herein, an "EPLIN-specific binding reagent" includes nucleic acids, such as probes, which hybridize to an EPLIN-specific cell component, such as DNA or RNA encoding the EPLIN protein. An EPLIN-specific binding reagent also includes proteins, such as antibodies, which bind to an EPLIN protein or fragment or derivative thereof. It is understood that an EPLIN-specific binding reagent includes any molecule which binds to an EPLIN-specific cell component such that the component can be identified.

One of the container means may comprise a probe which is or can be detectably labeled. Such probe may be an antibody or nucleotide specific for a target protein, or fragments thereof, or a target nucleic acid, or fragment thereof, respectively, wherein the target is indicative, or correlates with, the presence of EPLIN protein or EPLIN transcript. For example, oligonucleotide probes of the present invention can be included in a kit and used for examining the presence of EPLIN nucleic acid, as well as the quantitative (relative) degree of binding of the probe for determining the lack of binding (hybridizing) to the sequences, thus indicating the likelihood for an subject having a cell proliferation-associated pathology, such as, for example, cancer.

Where the kit utilizes nucleic acid hybridization to detect the target nucleic acid, the kit may also have containers containing nucleotide(s) for amplification of the target nucleic acid sequence. When it is desirable to amplify the target nucleic acid sequence, such as an EPLIN nucleic acid sequence, this can be accomplished using oligonucleotide(s) that are primers for amplification. For example, the kit may contain reagents necessary to perform RT-PCR on a sample containing, or suspected of containing, a cell harboring a pathogenic lentivirus such as HIV. Oligonucleotide primers based upon identification of the flanking regions contiguous with the target nucleotide sequence can be included in the kit such that the primers bind to an EPLIN transcript in the presence of, and under conditions that promote RT-PCR. The level of EPLIN transcript in a sample can be quantitated by means known to those of skill in the art.

The method of the invention provides the basis for a kit useful for the detection, or lack thereof, of a target EPLIN nucleic acid sequence in a sample obtained from a subject having, or suspected of having, a neoplasia. The absence, or under-production of, EPLIN transcript obtained from such a sample is indicative of the presence of a neoplasia. The kit includes a carrier means being compartmentalized to receive therein one or more containers. For example, a first container contains a nucleic acid primers which hybridize to the target nucleic acid (e.g, EPLIN RNA) for the purpose of performing semi-quantitative RT-PCR. In addition, the kit can provide a nucleic acid probe for detection of an EPLIN RNA transcript. Thus, a first container contains a nucleic acid hybridization probe which hybridizes to the target nucleic acid.

Other target nucleic acid sequences of EPLIN can be determined by those of skill in the art. In addition, the kit may include a second container containing a means for detecting hybridization of the probe with the target nucleic acid. Such reporter means include a biotin-binding protein, such as avidin or streptavidin, bound to a reporter molecule, such as an enzymatic, fluorescent, or radionuclide label. Other reporter means and labels are well known in the art. The kit may also include an amplification polymerase and deoxyribonucleotide(s). The kit may further include nucleic acid amplification buffer. Preferably, the reagent that modifies unmethylated cytosine is bisulfite. The kit of the invention is intended to provide the reagents necessary to perform nucleic acid hybridization analysis as described herein.

Techniques for obtaining a sample containing, or believed to contain, neoplastic cells are usually based on collection of tissues containing such cells. Such tissue can include, for example, blood, lymph or other tissue. However, it is understood that the method of the invention is useful for detecting a neoplasia in any sample believed to contain such cells. Sample acquisition can be accomplished by any means which allows for the isolation of a sample from a subject that results in a sufficient quantity of fluid being obtained for testing.

The kit may also include a container containing antibodies which bind to a target protein, or fragments thereof. Thus, it is envisioned that antibodies which bind to EPLIN, or fragments thereof, can be included in a kit. In addition, the kit may include a second container containing a means for detecting binding of the antibody with the target EPLIN protein, or fragment thereof. Such reporter means include a biotin-binding protein, such as avidin or streptavidin, bound to a reporter molecule, such as an enzymatic, fluorescent, or radionuclide label. Other reporter means and labels are well known in the art.

Gene Therapy Methods

It has been observed that certain tumor cells return to normal function when fused with normal cells, suggesting that replacement of a missing factor, such as a wild-type tumor suppressor gene expression product may serve to restore a tumor cell to a normal state. These observations have led to research aimed at providing genetic treatment of tumor cells having defective tumor suppressor genes. Thus, in another aspect, the invention provides a method for converting a neoplastic cell to a non-neoplastic state through the expression of wild-type levels of EPLIN.

Any of the methods known to the art for the insertion of DNA fragments into a vector, as described, for example, in Maniatis, T, Fritsch, E. F., and Sambrook, J. (1989): Molecular Cloning (a Laboratory manual), Cold Spring Harbor Laboratory, Cold Spring Harbor, New York; and Ausubel, F. M., Brent, R., Kingston, R. E., Moore, D. D., Seidman, J. G., Smith, J. a., and Struhl, K. (1992): Current Protocols in Molecular Biology, John Wiley & Sons, New York, may be used to construct EPLIN encoding gene expression vectors consisting of appropriate transcriptional/translational control signals and the desired EPLIN cDNA sequence downstream from the first in-frame AUG codon. These methods may include in vitro DNA recombinant and synthetic techniques and in vivo genetic recombination. Expression of a nucleic acid sequence encoding EPLIN may be regulated by a second nucleic acid sequence so that EPLIN is expressed in a host infected or transfected with the recombinant DNA molecule. For example, expression of EPLIN may be controlled by any promoter/enhancer element known in the art. The promoter activation may be tissue specific or inducible by a metabolic product or administered substance.

Promoters/enhancers which may be used to control EPLIN gene expression include, but are not limited to, the native EPLIN promoter, the cytomegalovirus (CMV) promoter/enhancer (Karasuyama, H. et al., 1989, *J. Exp. Med.*, 169:13), the human beta-actin promoter (Gunning, P. et al., 1987, *Proc. Natl. Acad. Sci. USA*, 84:4831), the glucocorticoid-inducible promoter present in the mouse mammary tumor virus long terminal repeat (HHTV LTR) (Klessig, D. F. et al., 1984, *Mol. Cell Biol.*, 4:1354), the long terminal repeat sequences of Moloney murine leukemia virus (MULV LTR) (Weiss, R. et al., 1985, RNA Tumor Viruses, Cold Spring Harbor Laboratory, Cold Spring Harbor, N.Y.), the SV40 early region promoter (Bernoist and Chambon, 1981, *Nature*, 290:304), the promoter contained in the 3' long terminal repeat of Rous sarcoma virus (RSV) (Yamamoto et al., 1980, *Cell* 22:787), the herpes simplex virus (HSV) thymidine kinase promoter/enhancer (Wagner et al., 1981, *Proc. Natl. Acad. Sci. U.S.A.*, 78:1441), the regulatory sequences of the metallothionein gene (Brinster et al., 1982, *Nature*, 296:39), the adenovirus promoter (Yamada et al., 1985, *Proc. Natl. Acad. Sci. USA.*, 82:3567), and the herpes simplex virus LAT promoter (Wolfe, J. H. et al., 1992, *Nature Genetics*, 1:379).

Expression vectors compatible with mammalian host cells for use in genetic therapy of tumor or cancer cells, include, but are not limited to: plasmids, retroviral vectors, adenovirus vectors, herpes viral vectors, and non-replicative avipox viruses, as disclosed, for example, by U.S. Pat. No. 5,174,993, incorporated herein by reference.

Methods of administering viral vectors are well known. In general, the skilled artisan will appreciate that a retroviral vector, an adenovirus vector, a plasmid vector, or any other appropriate vector capable of expressing the EPLIN protein can be administered in vivo to a neoplastic cell by a wide variety of manipulations. All such manipulations have in common the goal of placing the vector in sufficient contact with the target tumor to permit the vector to transduce or transfect the tumor cells. Neoplastic cells present in the epithelial linings of hollow organs may be treated by infusing the vector suspension into a hollow fluid filled organ, or by spraying or misting into a hollow air filled organ. Thus, the tumor cell may be present in or among the epithelial tissue in the lining of pulmonary bronchial tree, the lining of the gastrointestinal tract, the lining of the female reproductive tract, genitourinary tract, bladder, the gall bladder and any other organ tissue accessible to contact with the vector.

The EPLIN encoding gene construct of the present invention may be placed by methods well known to the art into an expression vector such as a plasmid or viral expression vector. A plasmid expression vector may be introduced into a tumor cell by calcium phosphate transfection, liposome (for example, LIPOFECTIN)-mediated transfection, DEAE Dextran-mediated transfection, polybrene-mediated transfection, electroporation and any other method of introducing DNA into a cell.

A viral expression vector may be introduced into a target cell in an expressible form by infection or transduction. Such a viral vector includes, but is not limited to: a retrovirus, an adenovirus, a herpes virus and an avipox virus. When EPLIN is expressed in any abnormally proliferating cell, the cell replication cycle is arrested, thereby resulting in senescence and cell death and ultimately, reduction in the mass of the abnormal tissue, i.e., the tumor or cancer. A vector able to introduce the gene construct into a target cell and able to express EPLIN therein in cell proliferation-suppressing amounts can be administered by any effective method.

For example, a physiologically appropriate solution containing an effective concentration of active vectors can be administered topically, intraocularly, parenterally, orally, intranasally, intravenously, intramuscularly, subcutaneously or by any other effective means. In particular, the vector may be directly injected into a target cancer or tumor tissue by a needle in amounts effective to treat the tumor cells of the target tissue.

Alternatively, a cancer or tumor present in a body cavity such as in the eye, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the cancer or tumor afflicted hollow organ. Any effective imaging device such as X-ray, soflogram, or fiberoptic visualization system may be used to locate the target tissue and guide the needle or catheter tube.

In another alternative, a physiologically appropriate solution containing an effective concentration of active vectors can be administered systemically into the blood circulation to treat a cancer or tumor that cannot be directly reached or anatomically isolated.

In yet another alternative, target tumor or cancer cells can be treated by introducing EPLIN protein into the cells by any known method. For example, liposomes are artificial membrane vesicles that are available to deliver drugs, proteins and plasmid vectors both in vitro or in vivo (Mannino, R. J. et al., 1988, *Biotechniques*, 6:682) into target cells (Newton, A. C. and Huestis, W. H., *Biochemistry*, 1988, 27:4655; Tanswell, A. K. et al., 1990, *Biochmica et Biophysica Acta*, 1044:269; and Ceccoll, J. et al., *Journal of Investigative Dermatology*, 1989, 93:190). Thus, EPLIN protein can be encapsulated at high efficiency with liposome vesicles and delivered into mammalian cells in vitro or in vivo.

Liposome-encapsulated EPLIN protein may be administered topically, intraocularly, parenterally, intranasally, intratracheally, intrabronchially, intramuscularly, subcutaneously or by any other effective means at a dose efficacious to treat the abnormally proliferating cells of the target tissue. The liposomes may be administered in any physiologically appropriate composition containing an effective concentration of encapsulated EPLIN protein.

In one embodiment a tumor cell is transduced with a retrovirus vector, an adenovirus vector, a plasmid vector or any other appropriate vector capable of expressing the EPLIN protein in that tumor cell. The cancer cell may be present in a blood or bone marrow sample collected from a leukemia patient. A dose of EPLIN protein expressing retrovirus vector or adenovirus vector or plasmid vector or any other appropriate vector is administered to the sample of blood or bone marrow at a dose sufficient to transduce enough cells in the sample to produce a reduction in tumor cell numbers. The cell proliferation of the treated cancer cells will be slowed or terminated followed by a process similar to normal cellular differentiation or cell senescence. Analogously, blood or bone marrow or other tissue is treated ex vivo using an effective dose of a liposome-encapsulated EPLIN protein. Thereafter the sample may be returned to the donor or infused into another recipient.

EXAMPLE 1

Materials and Methods

Cell Cultures

Human mammary epithelial cells (MEC) and normal human dermal fibroblasts were purchased from Clonetics. Breast cancer cell lines HBL-100, BT-20, SK-Br-3 and T-47D cells were cultured in RPMI 1640 medium supplemented with 10% fetal bovine serum (FBS) with T-47D cells receiving 1×ITS supplement (Sigma). MCF-7 and MDA-MB-231 cells were cultured in DMEM supplemented with 10% FBS. BeWo cells were cultured in Ham's F12K medium supplemented with 15% FBS.

Northern Blot Analysis and cDNA Cloning

10 μg total RNA isolated from cell cultures using RNA STAT-60 (Tel-Test) was used in Northern analysis as previously described (Chang et al., *Oncogene*, 16:1921, 1998). Filter membranes were probed with cDNA clone #21 (corresponding to amino acids 268–462 of EPLIN-β) and hybridization signals were quantified on a phosphorimager (Molecular Dynamics). All probes were labeled with [$^{32}$P]-α-dCTP using a random prime labeling kit (Stratagene). Multiple tissue mRNA blots was purchased from Clontech and used in hybridization following the manufacturer's protocol. The cDNA insert from clone #21 was used as a probe to isolate full length EPLIN-α and -β cDNAs from a HeLa cell cDNA library. Two representative clones were fully sequenced to obtain approximately 3.6 kb of sequence.

Antibodies and Protein Analysis

The carboxy terminal region of EPLIN (aa 680–759 of EPLIN-β) was cloned into the pQE-30 vector (Qiagen) and expressed as a 6xHis-tagged fusion protein in *E. coli* strain XL-1 Blue. The recombinant protein was purified on Ni-NTA agarose under native conditions following the manufacturer's recommendations and used as immunogen for polyclonal rabbit anti-EPLIN antibodies (Covance Research Products).

Cell lysates used in immunoblot analyses were prepared by boiling tissue culture cells or minced tissues in 0.2% SDS in TE (25 mM Tris-HCl, pH 7.5, 1 mM EDTA). 20 μg of cell lysates were separated by SDS-polyacrylamide gel electrophoresis and transferred to a nitrocellulose membrane. EPLIN isoforms were detected with polyclonal anti-EPLIN antibodies (1:10,000). To control the amounts of protein lysates, the filter membrane was also probed with a monoclonal anti-α-tubulin antibody (Sigma) at 1:2,000 dilution. Following incubation with a horseradish peroxidase-conjugated secondary antibody (Jackson ImmunoResearch), the immunoblots were developed using enhanced chemiluminescence (NEN).

Immunofluorescence

HOK18C and BeWo cells cultured on fibronectin-coated glass coverslips for 18 h were fixed in 3.7% formaldehyde (LADD Research) in PBS for 10 min and permeabilized in 0.2% Triton X-100 in PBS for 5 min. The slides were preincubated in a blocking buffer (0.1% Tween-20+10% goat serum in PBS) for 30 min before the addition of polyclonal anti-EPLIN antibodies (1:200 dilution). All incubations were performed at room temperature. HOK18C cells were labeled with Texas Red®-conjugated goat anti-rabbit IgG secondary antibody (Jackson ImmunoResearch) and Oregon Green® phalloidin (Molecular Probes) while BeWo cells were labeled with fluorescein isothiocyanate-conjugated goat anti-rabbit IgG secondary antibody (Jackson ImmunoResearch) and Texas Red® phalloidin (Molecular Probes). Coverslips were mounted with ProLong Antifade® (Molecular Probes) and viewed under a fluorescence microscope (Nikon). Pre-immune sera did not produce a staining pattern.

Conditional Expression of EPLIN

U2-OS cells were transfected with the plasmid pTet-On (Clontech) to create U2-OS Tet-On cells expressing tetracycline-inducible transactivator. EPLIN-α and -β cDNAs were cloned into the pTRE vector (Clontech) that has been modified by the insertion of an amino terminal FLAG epitope and multiple cloning sites. pTRE-FLAG-EPLIN-α or -β and pBABEpuro (Morgenstern and Land, *Nucleic Acids Res.*, 18:587, 1990) plasmids were co-transfected into the U2-OS cells and the stable transfectants were selected with puromycin (1 mg/ml). The expression of EPLIN in stable cell lines was induced by the addition of 0.5 mg/ml doxycycline (Sigma). Morphological changes were observed 48 h after the induction of EPLIN. Cell growth was determined by a tetrazolium dye colorimetric assay (Denizot and Lang, *J. Immunological Methods*, 89:271, 1986) with the following modifications. Cells were incubated for 3.5 h in phenol red-free RPMI 1640 medium (Sigma) with 1 mg/ml MTT (3-[4,5-dimethylthiazol-2-y]-2, 5-diphenyl tetrazolium bromid) (Sigma) and the formazan product was solubilized in isopropanol containing 0.04 N hydrochloric acid and 1% Triton X-100.

Figure 1B:
FIG. 1B shows the deduced amino acid sequence of EPLIN-α and EPLIN-β (SEQ ID NOs:2 (bottom) and 4 (top), respectively).

FIG. 1A is a schematic diagram of two EPLIN cDNAs. The sequence of two isoforms diverges at the 5' end (indicated by the stripped and dotted boxes). The EPLIN-β unique sequences allow the extension of the ORF by 160 aa at the amino terminus of EPLIN-α. The positions of in frame stop codons upstream to the AUG start codons for two EPLIN isoforms and the termination codons are denoted. FIG. 1B shows the deduced amino acid sequence of EPLIN-β. The ORF of EPLIN-α starts at aa position 161 of EPLIN-β. The aa sequences of two EPLIN isoforms are identical except for Arg344 of EPLIN-β which has been replaced by Pro184Gly185 in EPLIN-α. The 52 aa sequence of a LIM domain is underlined. FIG. 1C shows the alignment of the EPLIN LIM domain sequence with the LIM domain of the mutant SREBP-2, KIAA0750, plant transcription factor SF3, and muscle LIM protein. The signature cysteine and histidine residues of LIM domain are indicated by bold lettering. Amino acid sequence identities (o) and similarities (underlined) are indicated.

Figure 2A:
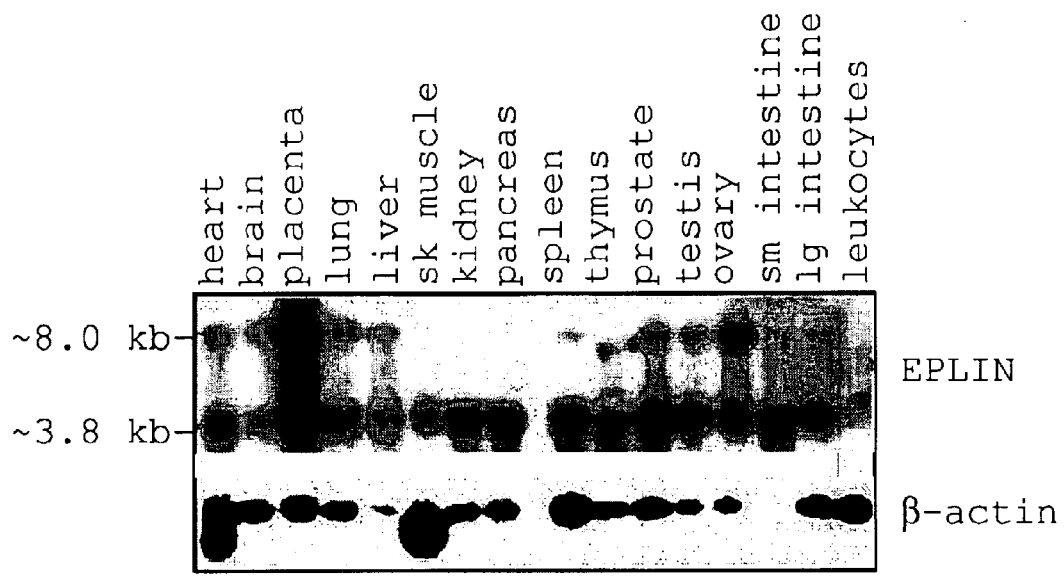
FIG. 2A shows that EPLIN is preferentially expressed in epithelial cells as determined by Northern analysis.

FIG. 2A shows the distribution of EPLIN expression in different human adult tissues as determined by a Northern analysis. Filters containing mRNA from multiple human tissues (Clontech) were used for Northern blotting. The positions of ~8 kb and ~3.8 kb transcripts hybridized by the EPLIN probe are indicated (top). The same blot was re-probed with human b-actin cDNA (bottom).

Figure 2B:
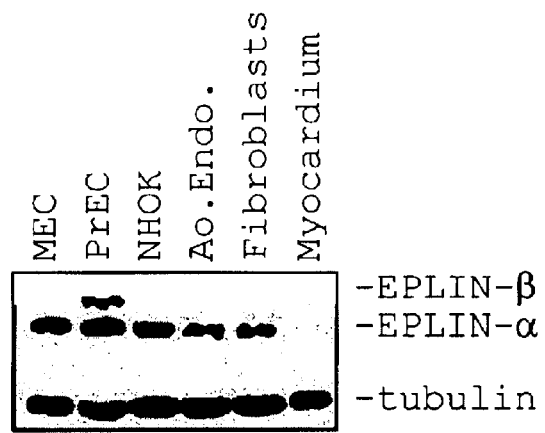
FIG. 2B shows the expression of EPLIN in different human primary cells by an immunoblot analysis.

FIG. 2B shows the expression of EPLIN in different human primary cells were examined by an immunoblot analysis. MEC: mammary epithelial cells. PrEC: prostate epithelial cells. NHOK: normal human oral keratinocytes. Ao. Endo.: aortic endothelial cells. Fibroblasts: Dermal fibroblasts. Myocardium: human left ventricle. The positions of EPLIN-α and -β are noted. The loading of equivalent amounts of cell lysates was confirmed by probing the filter membrane with anti-a tubulin antibody.

Figure 3A:
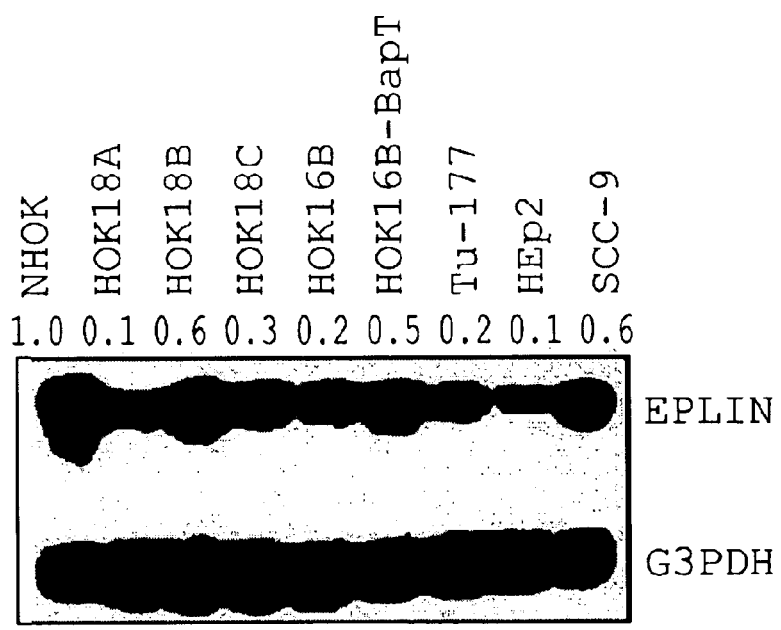
FIG. 3A shows, by Northern analysis, that the expression of EPLIN transcript is lost in epithelial cancer cells.
Figure 3B:
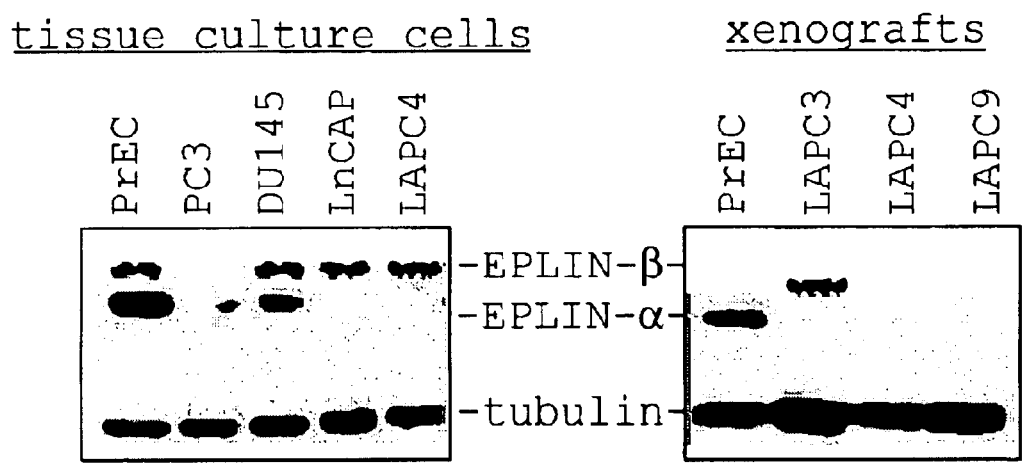
FIG. 3B shows the expression of EPLIN proteins in different prostate cancer cell lines and xenograft tumors as determined by an immunoblot analysis.
Figure 3C:
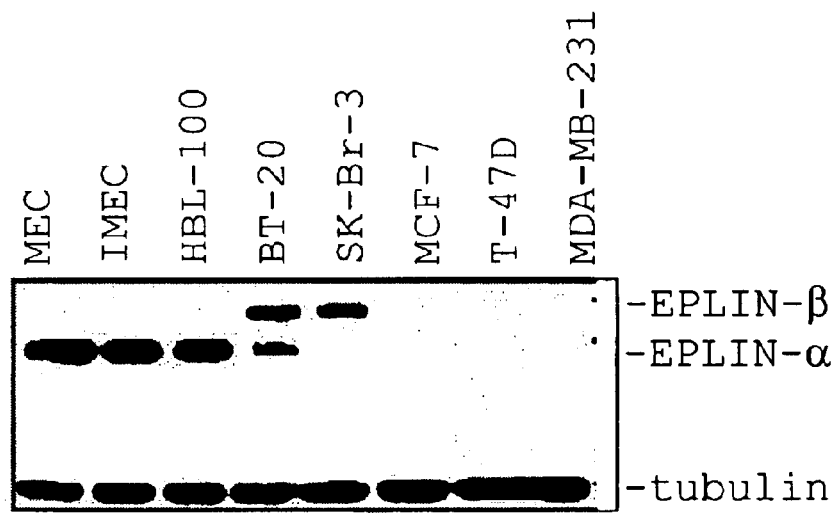
FIG. 3C shows the expression of EPLIN proteins in different breast cancer cell lines as determined by an immunoblot analysis.
Figure 3D:
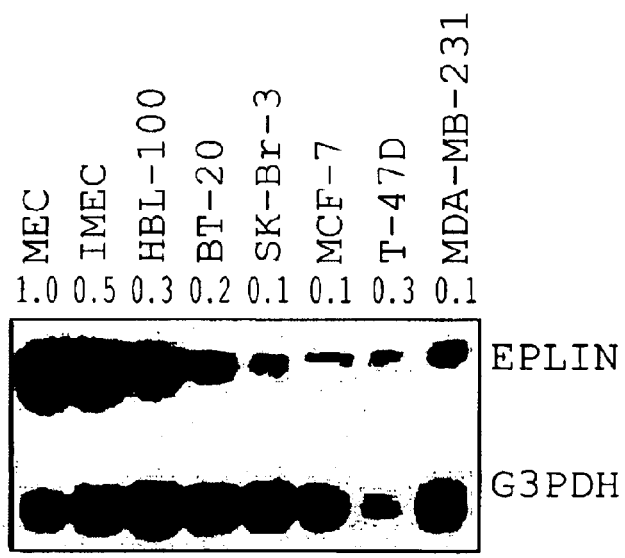
FIG. 3D shows the expression of EPLIN transcripts in different breast cancer cell lines as determined by a Northern analysis.

FIG. 3A shows the expression of EPLIN transcripts in HPV-immortalized oral keratinocyte cell lines (HOK18A–C and HOK16B), tumorigenic HPV-transformed oral keratinocyte cell line (HOK16B-BapT), and oropharyngeal cancer cells (Tu-177, HEp2, and SCC-9) was determined by a Northern analysis (top). The filter membrane was re-probed with human G3PDH cDNA (bottom). The expression of EPLIN, normalized against the G3PDH, in each cell line is indicated. FIG. 3B shows the expression of EPLIN proteins in different prostate cancer cell lines and xenograft tumors was determined by an immunoblot analysis. PrEC: prostate epithelial cells. PC3 and DU145: PSA-negative prostate cancer cell lines. LnCAP, LAPC3, LAPC4, and LAPC9: PSA-positive prostate cancer cells or xenograft tumors. The positions of EPLIN-α and -β are noted. The loading of equivalent amounts of cell lysates was confirmed by probing the filter membrane with anti-a tubulin antibody. FIG. 3C shows the expression of EPLIN proteins in different breast cancer cell lines was determined by an immunoblot analysis. MEC: mammary epithelial cells. IMEC: immortalized mammary epithelial cells. HBL-100 is a non-tumorigenic breast cancer cells, while BT-20, SK-Br-3, MCF-7, T-47D, and MDA-MB-231 are tumorigenic breast cancer cell lines. The positions of EPLIN-α and -β are noted. The loading of equivalent amounts of cell lysates was confirmed by probing the filter membrane with anti-a tubulin antibody. FIG. 3D shows the expression of EPLIN transcripts in different breast cancer cell lines was determined by a Northern analysis (top). The filter membrane was re-probed with human G3PDH cDNA (bottom). The expression of EPLIN, normalized against the G3PDH, in each cell line is indicated.

Figure 4A:
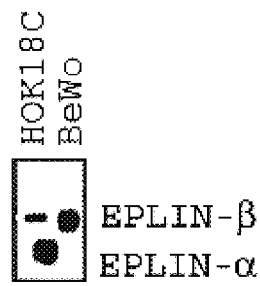
FIG. 4A shows the relative amount of EPLIN isoforms in HOK18C (a HPV-immortalized human oral keratinocyte cell line) and BeWo (a human choriocarcinoma cell line) as determined by an immunoblot analysis.

FIG. 4A shows the relative amount of EPLIN isoforms in HOK18C (an HPV-immortalized human oral keratinocyte cell line) and BeWo (a human choriocarcinoma cell line) was determined by an immunoblot analysis. EPLIN-α is expressed as the major isoform in HOK18C, while EPLIN-β is the major isoform in BeWo. FIG. B–E show the subcellular localization of EPLIN was determined by in situ immunofluorescence using anti-EPLIN antibodies (B and D). The staining pattern of anti-EPLIN antibodies (B and D) overlapped with the staining of actin stress fibers (C and E). Texas Red-conjugated goat anti-rabbit IgG secondary antibody (B) and fluorescein isothiocyanate-conjugated goat anti-rabbit IgG secondary antibody (D) were used to detect EPLIN. The stress fibers were stained with Oregon Green®-phalloidin and Texas Red®-phalloidin (E).

Figure 5A:
FIG. 5A shows U2-OS osteosarcoma cultured without expression of EPLIN-α.
Figure 5B:
FIG. 5B shows U2-OS osteosarcoma cultured with expression of EPLIN-α.
Figure 5C:
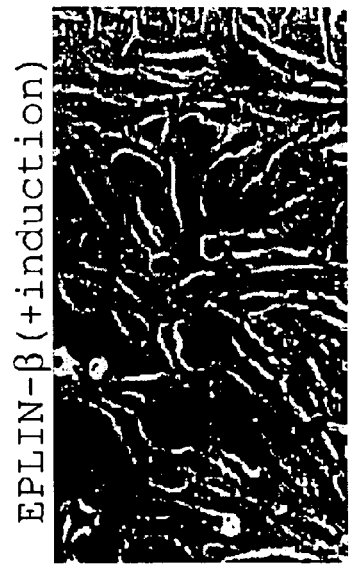
FIG. 5C shows U2-OS osteosarcoma cultured without expression of EPLIN-β.
Figure 5D:
FIG. 5D shows U2-OS osteosarcoma cultured with expression of EPLIN-β.
Figure 5E:
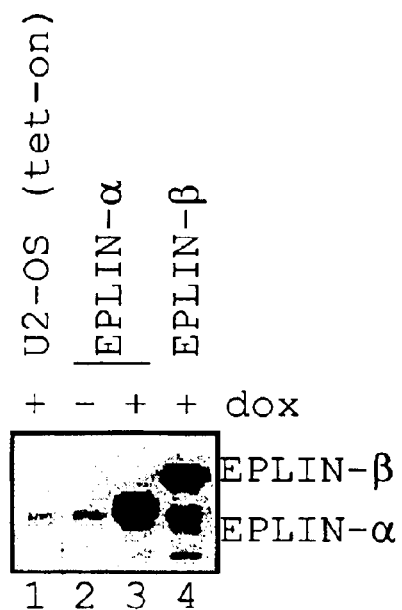
FIG. 5E shows the levels of EPLIN expression in the U2-OS cells cultures minus (no induction) and plus (induction) doxycycline as determined by an immunoblot analysis.
Figure 5F:
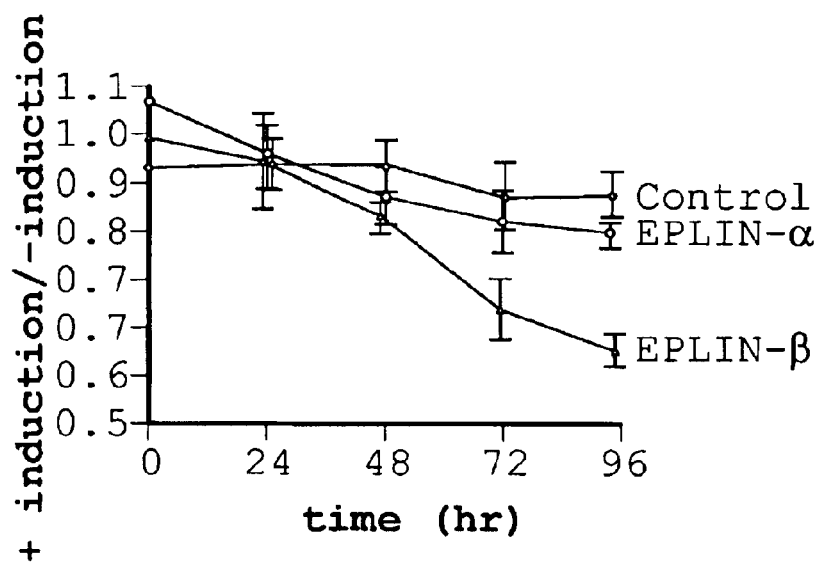
FIG. 5F shows the growth of U2-OS cells presented as the ratio of cell numbers with and without EPLIN induction.

FIGS. 5A–D show the U2-OS osteosarcoma cells were engineered to express either EPLIN-α or -β isoform under the control of a tetracycline-inducible promoter (Tet-On). The appearance of U2-OS cells cultured with (B and D) and without (A and C) the induction of EPLIN are shown. Note that the expression of EPLIN changed the morphology of the U2-OS cells from round polygonal cells to fusiform cells characterized by asymmetric cytoplasmic extensions. FIG. 5E shows the levels of EPLIN expression in the U2-OS cells cultures minus (no induction) and plus (induction) doxycycline were determined by an immunoblot analysis using anti-EPLIN antisera. Lane 1, parental U2-OS (Tet-on) cells; lane 2, U2-OS (EPLIN-α) cells before the induction; lane 3 and 4, U2-OS (EPLIN-α) and U2-OS (EPLIN-β) cells 48 h after the induction. FIG. 5F shows the growth of U2-OS cells is presented as the ratio of cell numbers with and without EPLIN induction. For each time point, cell growth in triplicates were determined by a tetrazolium dye inclusion method.

EXAMPLE 2 cDNA fragments containing a partial open reading frame (ORF) were identified by the presence of a LIM domain. Clone #21 was used as a probe to isolate several cDNA clones from a HeLa cell cDNA library. Sequence analysis of these cDNA clones allowed us to assemble an ORF of 600 aa (EPLIN-α) and an isoform (EPLIN-β) that extended an additional 160 aa at the amino terminus (FIG. 1A and 1B). The EPLIN-β mRNA also contained a deletion of 3 nucleotides within the coding region, introducing an Arg in place of ProGly at the corresponding position of EPLIN-α. Southern analysis indicated that EPLIN is a single copy gene, suggesting that the two EPLIN isoforms are generated by an alternative pre-RNA processing event. The predicted amino acid sequence of EPLIN was notable for a single centrally located LIM domain that is homologous to the partial ORF of a hamster gene of an unknown function. The EPLIN LIM domain is distantly related to the LIM domains of plant transcription factors SF-3 and the muscle LIM protein (FIG. 1C). Outside the LIM domain, EPLIN is unique in sequence, displaying no significant homology to known proteins or recognizable motifs.

Northern blot analysis of poly (a)+-RNA derived from normal human adult tissues demonstrated the expression of two EPLIN transcripts of ~3.8 kb and ~8 kb in size (FIG. 2A). The highest level of EPLIN mRNA was observed in placenta, followed by kidney, pancreas, prostate, ovary, spleen, and heart. A low level of EPLIN mRNA was also detected in all other tissues. The ORFs for both EPLIN-α and -β can be assembled from cDNA clones with insert sizes of ~3.6 kb, corresponding the —3.8 kb transcript seen on the Northern blot.

Polyclonal anti-EPLIN antisera directed against the carboxy-terminal region common to both α and β isoforms was prepared. In normal primary mammary (MEC), prostate (PrEC), and oral (NHOK) epithelial cells, anti-EPLIN antisera detected a major protein band of 90 kD and a second minor species of 110 kD in molecular weight (FIG. 2B). These two species were assigned EPLIN-α and EPLIN-β, respectively.

A Northern analysis of immortalized or transformed oropharyngeal cell lines confirmed a consistent down-regulation of EPLIN transcripts to 10 to 60% of the level seen in the NHOK (FIG. 3A). An immunoblot analysis demonstrated a reduction in EPLIN protein in these cell lines. Using anti-EPLIN antisera, we extended the expression analysis of EPLIN to different types of human cancers. An immunoblot analysis using cell lysates prepared from 4 human prostate cancer cell lines showed significant changes of EPLIN expression (FIG. 3B). In two PSA-negative prostate cancer cell lines, PC3 and DU145, EPLIN expression was detectable, but at significantly reduced levels compared to the level seen in the normal primary prostate epithelial cells (PrEC). In two PSA-positive prostate cancer cell lines, LnCap and LAPC4, the expression of EPLIN-α was not detectable, while EPLIN-β continued to be expressed at a level comparable to that in the PrEC. Examination of human prostate tumors propagated in SCID mice also demonstrated the loss of EPLIN-α expression in LAPC3, LAPC4, and LAPC9 xenografts.

A survey of breast cancer cell lines revealed a similar change in EPLIN expression (FIG. 3C). Both immortalized mammary epithelial cells (IMEC) and HBL-100, a non-tumorigenic breast cancer cell line, expressed EPLIN-α and -β isoforms at levels equivalent to that seen in the MEC. In the BT-20 breast cancer cells, there was a reduction in EPLIN-α accompanied by an increase in EPLIN-β. A similar increase EPLIN-β expression was also seen in the SK-Br-3 breast cancer cells which lacked the EPLIN-α expression. In three other breast cancer cell lines, EPLIN-α was either absent (MCF-7 and T-47D) or significantly reduced (MDA-MB-231), while EPLIN-β continued to be expressed at a level equivalent to that in the MEC. A Northern analysis demonstrated a reduction in EPLIN transcripts in all of the breast cancer cell lines, confirming that the loss of EPLIN proteins is due to a transcriptional down-regulation (FIG. 3D).

Figure 4B:
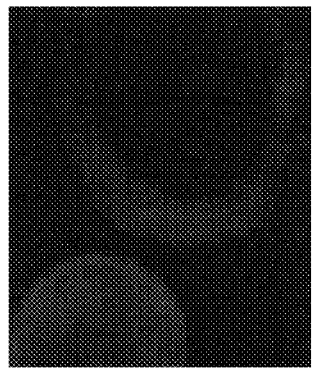
FIG. 4B shows the subcellular localization of EPLIN as determined by in situ immunofluorescence using anti-EPLIN antibodies and Texas Red®-conjugated goat anti-rabbit IgG secondary antibody.
Figure 4C:
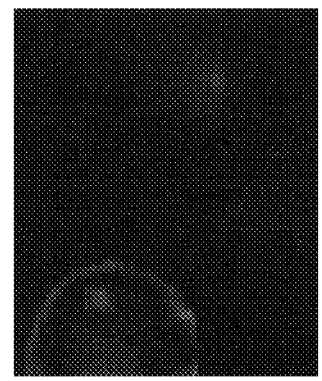
FIG. 4C shows the staining of actin stress fibers with Oregon Green®-phalloidin.
Figure 4D:
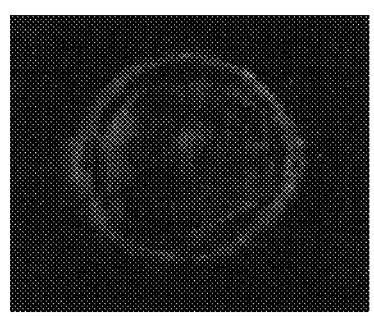
FIG. 4D shows the subcellular localization of EPLIN as determined by in situ immunofluorescence using anti-EPLIN antibodies and fluorescein isothiocyanate-conjugated goat anti-rabbit IgG secondary antibody.
Figure 4E:
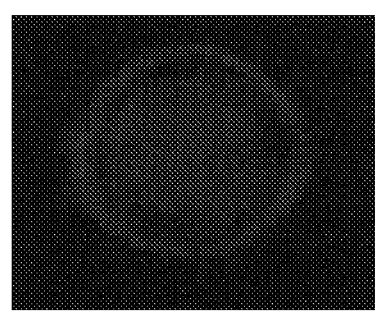
FIG. 4E shows the staining of actin stress fibers with Texas Red-phalloidin.

EPLIN is a cytoskelet al protein that can alter cell morphology and suppress cell proliferation. To investigate the potential function of EPLIN, the subcellular distribution of endogenous EPLIN was determined. Since the available polyclonal anti-EPLIN antisera do not distinguish the two known isoforms of EPLIN, in situ immunofluorescence was performed using two different cell lines, HOK18C (an immortalized human oral keratinocyte line) and BeWo (a human choriocarcinoma cell line). EPLIN-α is expressed as the predominant form in HOK18C, while EPLIN-β is the predominant form in BeWo (FIG. 4A). In situ immunofluorescence analysis demonstrated the localization of both EPLIN-α and -β to the cytoplasm in a fibrillar pattern at the periphery of the cell (FIG. 4B and D). This pattern of staining is similar to the staining of actin fibers with phalloidin (FIG. 4C and E). In addition, there was an overlap in the EPLIN staining to the paxillin staining (data not shown), suggesting that EPLIN is a component of the focal adhesion plaque.

To identify the effect of EPLIN on cell growth, each isoform was expressed in U2-OS osteosarcoma cells under the control of a tetracycline-inducible promoter. U2-OS cells, like most other cells, express EPLIN-α as the major isoform and a small amount of EPLIN-β isoform (FIG. 5E). Ectopic expression of either EPLIN isoform altered the morphology of the U2-OS cells from round polygonal cells with a cobblestone appearance to larger fusiform cells with spindle cell features and cytoplasmic extensions (FIGS. 5A–D). In addition, the EPLIN overexpressing cells required a longer incubation time in trypsin for detachment, suggesting a change in the cell-matrix interaction. An analysis of cell proliferation using a tetrazolium dye inclusion assay revealed that the induction of EPLIN-β suppresses cell growth (FIG. 5F). While the effect was not as pronounced, a growth inhibition was also seen when EPLIN-α was overexpressed.

The present invention provides a novel gene, EPLIN, that is down-regulated in human cancer cells. Although the expression of EPLIN varied considerably in different adult tissues, there was a general tendency of higher expression in tissues rich in epithelial cells. This preferential expression of EPLIN in epithelial cells was substantiated by an immunoblot analysis demonstrating high levels of EPLIN expression in the normal epithelial cells (e.g., MEC, PrEC, NHOK). Low levels of EPLIN were also detected in the primary aortic endothelial cells and fibroblasts, but not in the myocardium. The absence of EPLIN proteins in the myocardium, in view of the relative abundance of EPLIN transcripts in the same tissue, suggest that the steady state level of EPLIN proteins can be subjected to a posttranslational regulation. The reduction in EPLIN protein in cancer cells in general paralleled the reduction in EPLIN transcripts (see FIG. 3C and D).

EPLIN sequence analysis revealed a single centrally located LIM domain. This motif may allow EPLIN to interact with other cellular proteins. Several LIM domain proteins have been implicated in cellular transformation. LMO-2 (formerly called RBTN2/TTG2), which interacts with the basic-helix-loop-helix protein Tal/Scl, is aberrantly expressed in acute T-cell leukemia as a result of chromosomal rearrangement and can promote T-cell tumors (Rabbitts, *Genes and Devel.*, 12:2651, 1998). ril and DRAL are proteins of unknown function that are transcriptionally down-regulated in Ras-transformed cells and rhabdomyosarcoma cells, respectively (Kiess et al., *Oncogene*, 10:61, 1995; Genini et al., *DNA and Cell Biol.*, 16:433, 1997). Many LIM domain proteins are involved in cell lineage determination as DNA-binding transcription factors or accessory factors that associate with DNA-binding transcription factors to modulate gene transcription (Dawid et al., *Trends in Genetics*, 14:156, 1998). Other LIM domain proteins interact with cytoskelet al proteins or localize to the site of cell-matrix attachment. This class of LIM domain proteins includes zyxin (Beckerle, *Bioessays*, 19:949, 1997); paxillin, hic-5, and leupaxin (Brown et al., *J. Cell Biol.*, 135:1109, 1996); LIM-kinase (Yang et al., *J. Biol. Chem.*, 270:12152, 1998); and limatin (Roof et al., *J. Cell Biol.*, 138:575, 1997). The amino acid sequence of the EPLIN LIM domain is closely related to the LIM domain of the plant transcription factor SF3 (48% aa identity; 73% aa similarity within the 52 aa LIM domain).

In situ immunofluorescence studies showed localization of both EPLIN-α and -β isoforms to filamentous actin-rich areas at the periphery of the cell. Furthermore, there was a frequent overlap between EPLIN staining and paxillin staining, suggesting that EPLIN maybe present in the focal adhesion plaques as well. The overexpression of EPLIN appears to affect the cell-matrix interactions as evidenced by changes in cell morphology. While the subcellular localization of endogenous EPLIN-α and -β isoforms was indistinguishable, ectopic expression of EPLIN-β had a more pronounced effect on the growth of U2-OS cells, suggesting a potential functional difference between the two EPLIN isoforms.

EPLIN expression is down-regulated in the majority of cancer cell lines examined in the present study, indicating that the loss of EPLIN expression is directly linked to cellular transformation. Breast and prostate cancer cells, but not the oropharyngeal cancer cells, exhibited a specific loss of EPLIN-α isoform. The loss of EPLIN-α isoform was accompanied by an increase in EPLIN-β isoform in 2/6 breast cancer cell lines (e.g., BT-20 and SK-Br-3). The combined levels of the two EPLIN isoforms were lower in BT-20 and SK-Br-3 cells.

The major difference between the two EPLIN isoforms is at the amino terminus where the b isoform contains an extension of 160 aa. The sequence divergence may be an alternative pre-mRNA splicing event involving a single pre-mRNA that utilizes alternative exons. Alternatively, EPLIN is transcribed from two distinct promoters to generate two pre-mRNA species both of which are spliced to the common 3' exons. The relative increase in EPLIN-β in breast cancer cell lines BT-20 and Sk-Br-3, which have lost the expression of EPLIN-α, indicates that the expression of the two EPLIN isoforms can be regulated independently.

EPLIN-α Nucleic Acid Sequence (SEQ ID NO:1)

gctttctccatgtggcaaggctgtaactgttcacagctgtctgaaacagcagtggaccaggagcagcttggagttttaactttcattttaca aagaacaacatgtttgaatgtttcagcaggcaagttataactggcatctacttcttgttcttctagaacaccgaaaatctctcccagcacttt agaaaggggaccctgactgtgttaaagaagaagtgggagaacccagggctgggagcagagtctcacacagactctctacggaaca gcagcactgagattaggcacagagcagaccatcctcctgctgaagtgacaagccacgctgcttctggagccaaagctgaccaagaa gaacaaatccacccagatctagactcaggtcacctcctgaagccctcgttcagggtcgatatcccacatcaaggacggtgaggatc ttaaagaccactcaacagaaagtaaaaaaATGGAAAATTGTCTAGGAGAATCCAGGCATGAAGTAG

AAAAATCAGAAATCAGTGAAAACACAGATGCTTCGGGCAAAATAGAGAAATATAA

TGTTCCGCTGAACAGGCTTAAGATGATGTTTGAGAAAGGTGAACCAACTCAAACT

AAGATTCTCCGGGCCCAAAGCCGAAGTGCAAGTGGAAGGAAGATCTCTGAAAAC

AGCTATTCTCTAGATGACCTGGAAATAGGCCCAGGTCAGTTGTCATCTTCTACATTT

GACTCGGAGAAAAATGAGAGTAGACGAAATCTGGAACTTCCACGCCTCTCAGAA

ACCTCTATAAAGGATCGAATGGCCAAGTACCAGGCAGCTGCGTCCAAACAAAGCA

GCTCAACCAACTATACAAATGAGCTGAAAGCCAGTGGTGGCGAAATCAAAATTCA

TAAAATGGAGCAAAAGGAGAATGTGCCCCCAGGTCCTGAGGTCTGCATCACCCAT

CAGGAAGGGGAAAAGATTTCTGCAAATGAGAATAGCCTGGCAGTCCGTTCCACCC

CTGCCGAAGATGACTCCCCAGGTGACTCCCAGGTTAAGAGTGAGGTTCAACAGC

CTGTCCATCCCAAGCCACTAAGTCCAGATTCCAGAGCCTCCAGTCTTTCTGAAAG

TTCTCCTCCCAAAGCAATGAAGAAGTTTCAGGCACCTGCAAGAGAGACCTGCGT

GGAATGTCAGAAGACAGTCTATCCAATGGAGCGTCTCTTGGCCAACCAGCAGGTG

TTTCACATCAGCTGCTTCCGTTGCTCCTATTGCAACAACAAACTCAGTCTAGGAAC

ATATGCATCTTTACATGGAAGAATCTATTGTAAGCCTCACTTCAATCAACTCTTTAA

ATCTAAGGGCAACTATGATGAAGGCTTTGGGCACAGACCACACAAGGATCTATGG

GCAAGCAAAAATGAAAACGAAGAGATTTTGGAGAGACCAGCCCAGCTTGCAAAT

GCAAGGGAGACCCCTCACAGCCCAGGGGTAGAAAATGCCCCTATTGCTAAGGTG

GGTGTCCTGGCTGCAAGTATGGAAGCCAGGGCCTCCTCTCAGCAGGAGAAGGAA

GACAAGCCAGCTGAAACCAAGAAGCTGAGGATCGCCTGGCCACCCCCCACTGAA

CTTGGAAGTTCAGGAAGTGCCTTGGAGGAAGGGATCAAAATGTCAAAGCCCAAA

TGGCCTCCTGAAGACGAAATCAGCAAGCCCGAAGTTCCTGAGGATGTCGATCTAG

ATCTGAAGAAGCTAAGACGATCTTCTTCACTGAAGGAAAGAAGCCGCCCATTCAC

TGTAGCAGCTTCATTTCAAAGCACCTCTGTCAAGAGCCCAAAAACTGTGTCCCCA

CCTATCAGGAAAGGCTGGAGCATGTCAGAGCAGAATGAAGAATCTGTGGGTGGA

AGAGTTGCAGAAAGGAAACAAGTGGAAAATGCCAAGGCTTCTAAGAAGAATGGG

AATGTGGGAAAAACAACCTGGCAAAACAAAGAATTTAAAGGAGAGACAGGGAA

GAGAAGTAAGGAAGGTCATAGTTTGGAGATGGAGAATGAGAATTTTGTAGAAAAT

-continued

```
GGTGCAGACTCCGATGAAGATGATAACAGCTTCCTCAAACAACAATTTCCACAAG

AACCCAAGTTTTTGAATTGGTCGAGTTTTGTAGACAACACCTTTGCTGAAGAATTC

ACTACTCAGAATCAGAAATCCCAGGATGTGGAACTTTGGGAGGGAGAAGTGGTC

AAAGAGCTCTCTGTGGAAGAACAGATAAAGAGAAATCGGTATTATGATGAGGATG

AGGATGAAGAGTGAcaaattgcaatgatgctgggccttaaattcatgttagtgttagcgagccactgcccttttgtcaaaatg tgatgcacataagcaggtatcccagcatgaaatgtaatttacttggaagtaactttggaaaagaattccttcttaaaatcaaaaacaaaac aaaaaaacacaaaaaacacattctaaatactagagataactttacttaaattcttcatcagtgatgatatgcataagtgctgtaaggcttgta actggggaaatattccacctgataatagcccagattctactgtattcccaaaaggcaatattaaggtagatagatgattagtagtatattgtt acacactattttggaattagagaacatacagaaggaatttaggggcttaaacattacgactgaatgcactttagtataaagggcacagttt gtatattttaaatgaataccaatttaattttttagtatttacctgttaagagattatttagtctttaaattttttaggttaattttcttgctgtgatatat atgaggaatttactactttatgtcctgctctctaaactacatcctgaactcgacgtcctgaggtataacaacagagcacttttttgaggcaatt gaaaaaccaacctacactcttcggtgcttagagagatctgctgtctcccaaataagcttttgtatctgccagtgaatttactgtactccaaat gattgctttcttttctggtgatatctgtgcttctcataattactgaaagctgcaatattttagtaataccttcgggatcactgtccccatcttcc gtgttagagcaaagtgaagagtttaaaggaggaagaagaaagaactgtcttacaccacttgagctcagacctctaaaccctgtatttcc cttatgatgtcccctttttgagacactaattttaaatacttactagctctgaaatatattgattttatcacagtattctcagggtgaaattaaac caactataggccttttttcttgggatgattttctagtcttaaggtttggggacattataaacttgagtacatttgttgtacagttgatattccaa attgtatggatgggagggagaggtgtcttaagctgtaggcttttctttgtactgcatttatagagatttagctttaatatttttttagagatgtaa aacattctgctttcffagtcttacctagtctgaaacatttttattcaataaagattttaattaaaatttg
```

EPLIN-α Amino Acid Sequence (SEQ ID NO:2)

```
MENCLGESRHEVEKSEISENTDASGKIEKYNVPLNRLKMMFEKGEPTQTKILRAQSRSAS

GRKISENSYSLDDLEIGPGQLSSSDSEKNESRRNLELPRLSETSIKDRMAKYQAAVSK

QSSSTNYTNELKASGGEIKIHKMEQKENVPPGPEVCITHQEGEKISANENSLAVRSTPAE

DDSPGDSQVKSEVQQPVHPKPLSPDSRASSLSESSPPKAMKKFQAPARETCVECQKTVYP

MERLLANQQVFHISCFRCSYCNNKLSLGTYASLHGRIYCKPHFNQLFKSKGNYDEGFGHR

PHKDLWASKNENEEILERPAQLANARETPHSPGVEDAPIAKVGVLAASMEAKASSQQEKE

DKPAETKKLRIAWPPPTFLGSSGSALEEGIKMSKPKWPPEDEISKPEVPEDVDLDLKKLR

RSSSLKERSRPFTVAASFQSTSVKSPKTVSPPIRKGWSMSEQSEESVGGRVAERKQVENA

KASKKNGNVGKJTWQNKEsSKGETGKRSKEGHSLEMENEHVENGADSDEDDNSFLKQQsSP

QEPKsSLNWSSFVDNTFAEEFTTQNQKSQDVELWEGEVVKELSVEEQIKRNRYYDEDEDEE
```

EPLIN-β Nucleic Acid Sequence (SEQ ID NO:3)

```
ggcacgaggcgctaggtagagcgccgggacctgtgacagggctggtagcagcgcacaggaaaggcggcttttagccaggtatttcagt gtctgtagacaagATGGAATCATCTCCATTTAATAGACGGCAATGGACCTCACTATCATTGAG

GGTAACAGCCAAAGAACTTTCTCTTGTCAACAAGAACAAGTCATCGGCTATTGTGGA

AATATTCTCCAAGTACCAGAAAGCAGCTGAAGAAACAAACATGGAGAAGAAGAGAA

GTAACACCGAAAATCTCTCCCAGCACTTTAGAAAGGGGACCCTGACTGTGTTAAAGA

AGAAGTGGGAGAACCCAGGGCTGGGAGCAGAGTCTCACACAGACTCTCTACGGAAC

AGCAGCACTGAGATTAGGCACAGAGCAGACCATCCTCCTGCTGAAGTGACAAGCCA

CGCTGCTTCTGGAGCCAAAGCTGACCAAGAAGAACAAATCCACCCCAGATCTAGACT

CAGGTCACCTCCTGAAGCCCTCGTTCAGGGTCGATATCCCCACATCAAGGACGGTGA

GGATCTTAAAGACCACTCAACAGAAAGTAAAAAAATGGAAAATTGTCTAGGAGAATC
```

-continued

```
CAGGCATGAAGTAGAAAAATCAGAAATCAGTGAAAACACAGATGCTTCGGGCAAAAT
AGAGAAATATAATGTTCCGCTGAACAGGCTTAAGATGATGTTTGAGAAAGGTGAACC
AACTCAAACTAAGATTCTCCGGGCCCAAAGCCGAAGTGCAAGTGGAAGGAAGATCT
CTGAAAACAGCTATTCTCTAGATGACCTGGAAATAGGCCCAGGTCAGTTGTCATCTTC
TACATTTGACTCGGAGAAAAATGAGAGTAGACGAAATCTGGAACTTCCACGCCTCTC
AGAAACCTCTATAAAGGATCGAATGGCCAAGTACCAGGCAGCTGCGTCCAAACAAAG
CAGCTCAACCAACTATACAAATGAGCTGAAAGCCAGTGGTGGCGAAATCAAAATTCA
TAAAATGGAGCAAAAGGAGAATGTGCCCCCAGGTCCTGAGGTCTGCATCACCCATCA
GGAAGGGGAAAAGATTTCTGCAAATGAGAATAGCCTGGCAGTCCGTTCCACCCCTGC
CGAAGATGACTCCCCAGGTGACTCCCAGGTTAAGAGTGAGGTTCAACAGCCTGTCCA
TCCCAAGCCACTAAGTCCAGATTCCAGAGCCTCCAGTCTTTCTGAAAGTTCTCCTCCC
AAAGCAATGAAGAAGTTTCAGGCACCTGCAAGAGAGACCTGCGTGGAATGTCAGAA
GACAGTCTATCCAATGGAGCGTCTCTTGGCCAACCAGCAGGTGTTTCACATCAGCTG
CTTCCGTTGCTCCTATTGCAACAACAAACTCAGTCTAGGAACATATGCATCTTTACATG
GAAGAATCTATTGTAAGCCTCACTTCAATCAACTCTTTAAATCTAAGGGCAACTATGAT
GAAGGCTTTGGGCACAGACCACACAAGGATCTATGGGCAAGCAAAAATGAAAACGA
AGAGATTTTGGAGAGACCAGCCCAGCTTGCAAATGCAAGGGAGACCCCTCACAGCC
CAGGGGTAGAAAATGCCCCTATTGCTAAGGTGGGTGTCCTGGCTGCAAGTATGGAAG
CCAGGGCCTCCTCTCAGCAGGAGAAGGAAGACAAGCCAGCTGAAACCAAGAAGCT
GAGGATCGCCTGGCCACCCCCCACTGAACTTGGAAGTTCAGGAAGTGCCTTGGAGG
AAGGGATCAAAATGTCAAAGCCCAAATGGCCTCCTGAAGACGAAATCAGCAAGCCC
GAAGTTCCTGAGGATGTCGATCTAGATCTGAAGAAGCTAAGACGATCTTCTTCACTGA
AGGAAAGAAGCCGCCCATTCACTGTAGCAGCTTCATTTCAAAGCACCTCTGTCAAGA
GCCCAAAAACTGTGTCCCCACCTATCAGGAAAGGCTGGAGCATGTCAGAGCAGAATG
AAGAATCTGTGGGTGGAAGAGTTGCAGAAAGGAAACAAGTGGAAAATGCCAAGGCT
TCTAAGAAGAATGGGAATGTGGGAAAAACAACCTGGCAAAACAAAGAATTTAAAGG
AGAGACAGGGAAGAGAAGTAAGGAAGGTCATAGTTTGGAGATGGAGAATGAGAATT
TTGTAGAAAATGGTGCAGACTCCGATGAAGATGATAACAGCTTCCTCAAACAACAAT
TTCCACAAGAACCCAAGTTTTTGAATTGGTCGAGTTTTGTAGACAACACCTTTGCTGA
AGAATTCACTACTCAGAATCAGAAATCCCAGGATGTGGAACTTTGGGAGGGAGAAGT
GGTCAAAGAGCTCTCTGTGGAAGAACAGATAAAGAGAAATCGGTATTATGATGAGGA
TGAGGATGAAGAGTGAcaaattgcaatgtatgctgggccttaaattcatgttagtgttagcgagccactgccctttgtcaaaatgt
gatgcacataagcaggtatcccagcatgaaatgtaatttacttggaagtaactttggaaaagaattccttcttaaaatcaaaaacaaaacaaaa
aaacacaaaaaacacattctaaatactagagataactttacttaaattcttcatcagtgatgatatgcataagtgctgtaaggcttgtaactgggg
aaatattccacctgataatagcccagattctactgtattcccaaaaggcaatattaaggtagatagatgattagtagtatattgttacacactatttt
ggaattagagaacatacagaaggaatttaggggcttaaacattacgactgaatgcacttagtataaagggcacagtttgtatattaaatgaa
taccaatttaatttttttagtatttacct-
gttaagagattatttagtctttaaattttttaggttaatttttcttgctgtgatatatatgaggaatttactactttat
gtcctgctctctaaactacatcctgaactcgacgtcctgaggtataacaacagagcacttttttgaggcaattgaaaaaccaacctacactcttc
ggtgcttagagagatctgctgtctcccaaataagcttttgtatctgccagtgaatttactgtactccaaatgattgctttcttttctggtgatatctgt
```

-continued

```
gcttctcataattactgaaagctgcaatattttagtaataccttcgggatcactgtcccccatcttccgtgttagagcaaagtgaagagtttaaag gaggaagaagaaagaactgtcttacaccacttgagctcagacctctaaaccctgtatttcccttatgatgtcccctttttgagacactaatttttaa atacttactagctctgaaatatattgattttatcacagtattctcagggtgaaattaaaccaactataggccttttcttgggatgattttctagtctta aggtttggggacattataaacttgagtacatttgttgtacacagttgatattccaaattgtatggatgggagggagaggtgtcttaagctgtagg cttttctttgtactgcatttatagagatttagctttaatattttttagagatgtaaaacattctgctttcttagtcttacctagtctgaaacattttattcaa taaagattttaattaaaatttg
```

EPLIN-β Amino acid Sequence (SEQ ID NO:4)

MESSPFNRRQWTSLSLRVTAKELSLVNKNKSSAIVEIFSKYQKAAEETNMEKKRSNTENL

SQHFRKGTLTVLKKKWENPGLGAESHTDSLRNSSTEIRHRADHPPAEVTSHAASGAKADQ

EEQIHPRSRLRSPPEALVQGRYPHIKDGEDLKDHSTESKKMENCLGESRHEVEKSEISEN

TDASGKIEKYNVPLNRLKMMFEKGEPTQTKILRAQSRSASGRKISENSYSLDDLEIGPGQ

LSSSTFDSEKNESRRNLELPRLSETSIKDRMAKYQAAVSKQSSSTNYTNELKASGGEIKI

HKMEQKENVPPGPEVCITHQEGEKISANENSLVRSTPAEDDSRDSQVKSEVQQPVHPKP

LSPDSRASSLSESSPPKAMKKFQAPARETCVECQKTVYPMERLLANQQVFHISCFRCSYC

NNKLSLGTYASLHGRIYCKPHFNQLFKSKGNYDEGFGHRPHKDLWASKNENEEWERPAQ

LANARETPHSPGVEDAPIAKVGVLAASMEAKASSQQEKEDKPAETKKLRIAWPPPTELGS

SGSALEEGIKMSKPKWPPEDEISKPEVPEDVDLDLKKLRRSSSLKERSRPFTVAASFQST

SVKSPKTVSPPIRKGWSMSEQSEESVGGRVAERKQVENAKASKKNGNVGKTTWQNKEsSKG

ETGKRSKEGRSLEMENEN1VENGADSDEDDNSFLKQQsSPQEPKsSLNWSSFVDNTFAEEFT

TQNQKSQDVELWEGEVVKELSVEEQIKRNRYYDEDEDEE

It will be apparent to those skilled in the art that various modifications and variations can be made to the compositions and processes of this invention. Thus, it is intended that the present invention cover such modifications and variations, provided they come within the scope of the appended claims and their equivalents.

---

What is claimed is:

1. An isolated nucleic acid comprising the nucleotide sequence of SEQ ID NO:3.

2. An isolated nucleic acid consisting of the nucleotide sequence of SEQ ID NO:3.

3. An isolated nucleic acid comprising a sequence at least 95% identical to SEQ ID NO:3 or SEQ ID NO:10, wherein ectopic expression of the polypeptide encoded by said nucleic acid in U2-OS cells;

(a) alters the morphology of the cells from round polygonal cells to larger fusiform cells with spindle cell features and cytoplasmic extensions; and (b) suppresses U2-OS cell growth.

4. The nucleic acid of claim 3, wherein the sequence is at least 97% identical to SEQ ID NO:3 or SEQ ID NO:10.

5. The nucleic acid of claim 3, wherein the sequence is at least 99% identical to SEQ ID NO:3 or SEQ ID NO:10.

6. An isolated nucleic acid comprising a cDNA or RNA encoding a polypeptide comprising an amino acid sequence at least 90% identical to SEQ ID NO:4, wherein ectopic expression of the polypeptide encoded by said nucleic acid in U2-OS cells;

(a) alters the morphology of the cells from round polygonal cells to larger fusiform cells with spindle cell features and cytoplasmic extensions; and (b) suppresses U2-OS cell growth.

7. The nucleic acid of claim 6, wherein the amino acid sequence is at least 95% identical to SEQ ID NO:4.

8. An isolated nucleic acid comprising a cDNA or RNA encoding a polypeptide comprising the amino acid sequence of SEQ ID NO:4, with up to 50 conservative amino acid substitutions, wherein ectopic expression of the polypeptide encoded by said nucleic acid in U2-OS cells;

(a) alters the morphology of the cells from round polygonal cells to larger fusiform cells with spindle cell features and cytoplasmic extensions; and (b) suppresses U2-OS cell growth.

9. The isolated nucleic acid of claim 8, wherein the amino acid sequence of SEQ ID NO:4 comprises up to 20 conservative amino acid substitutions.

10. An isolated nucleic acid comprising a cDNA or RNA encoding a polypeptide comprising the amino acid sequence of SEQ ID NO:4, or immunogenic fragment of SEQ ID NO:4 at least 10 residues in length, wherein ectopic expression of the polypeptide encoded by said nucleic acid in U2-OS cells;

(a) alters the morphology of the cells from round polygonal cells to larger fusiform cells with spindle cell features and cytoplasmic extensions; and (b) suppresses U2-OS cell growth;

wherein said immunogenic fragment is capable of eliciting the production of an antibody that binds specifically to the polypeptide of SEQ ID NO: 4.

11. The isolated nucleic acid of claim 10, wherein the immunogenic fragment comprises residues 680–759 of SEQ ID NO:4.

12. An isolated nucleic acid comprising a sequence that hybridizes under highly stringent conditions to a hybridization probe the sequence of which encodes the polypeptide of SEQ ID NO:4, or the full complement thereof, wherein said highly stringent conditions comprise hybridization in 6×sodium chloride/sodium citrate (SSC) at about 45° C., followed by one or more washes in 0.2×SSC, 0.1% SDS at 65° C., wherein ectopic expression of the polypeptide encoded by said nucleic acid in U2-OS cells;

(a) alters the morphology of the cells from round polygonal cells to larger fusiform cells with spindle cell features and cytoplasmic extensions; and (b) suppresses U2-OS cell growth.

13. An isolated nucleic acid comprising a sequence that hybridizes under highly stringent conditions to a hybridization probe the sequence of which consists of SEQ ID NO:3, excluding residues 3,097 to 3,458, or SEQ ID NO:10, or to the full complement of SEQ ID NO:3, excluding residues 3,097 to 3,458, or SEQ ID NO:10, wherein said highly stringent conditions comprise hybridization in 6×sodium chloride/sodium citrate (SSC) at about 45° C., followed by one or more washes in 0.2×SSC, 0.1% SDS at 65° C., wherein ectopic expression of the polypeptide encoded by said nucleic acid in U2-OS cells;

(a) alters the morphology of the cells from round polygonal cells to larger fusiform cells with spindle cell features and cytoplasmic extensions; and (b) suppresses U2-OS cell growth.

14. An isolated nucleic acid comprising the nucleotide sequence of SEQ ID NO:10, or degenerate variant of SEQ ID NO:10, which degenerate variant encodes a polypeptide comprising the amino acid sequence of SEQ ID NO:4.

15. An expression vector comprising a nucleic acid of claim 1, 2, 3, 6, 8, 10, 12, 13 or 14.

16. The expression vector of claim 15, wherein the vector is a plasmid.

17. The expression vector of claim 15, wherein the vector is a viral vector.

18. An isolated host cell transformed with an expression vector of claim 15.

19. The host cell of claim 18, wherein the cell is a eukaryotic cell.

20. The host cell of claim 18, wherein the cell is a prokaryotic cell.

21. A method of producing a polypeptide comprising:

(a) transforming a host cell with a nucleic acid of claim 1, 2, 3, 6, 8, 10, 12, 13, or 14, wherein said polypeptide is encoded by said nucleic acid; and (b) expressing the nucleic acid in the host, wherein the polypeptide is produced.

22. The method of claim 21, wherein the host cell is a prokaryotic cell.

23. The nucleic acid of claim 6, 8, or 10, wherein the polypeptide is the polypeptide of SEQ ID NO:4.

* * * * *